United States Patent
Usagawa

(10) Patent No.: US 7,541,811 B2
(45) Date of Patent: Jun. 2, 2009

(54) APPARATUS FOR ELECTRON SPIN RESONANCE CT

(75) Inventor: Toshiyuki Usagawa, Saitama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/774,273

(22) Filed: Jul. 6, 2007

(65) Prior Publication Data

US 2008/0061782 A1    Mar. 13, 2008

(30) Foreign Application Priority Data

Sep. 11, 2006    (JP) .............................. 2006-245597

(51) Int. Cl.
*G01V 3/00* (2006.01)
(52) U.S. Cl. ...................... 324/319; 324/320
(58) Field of Classification Search ................. 324/319, 324/320
See application file for complete search history.

(56) References Cited

U.S. PATENT DOCUMENTS

| | | | | |
|---|---|---|---|---|
| 4,818,966 A | * | 4/1989 | Miyamoto et al. | 335/296 |
| 5,097,240 A | * | 3/1992 | Nakanishi et al. | 335/296 |
| 5,218,333 A | * | 6/1993 | Kobayashi | 335/296 |
| 7,084,632 B2 | * | 8/2006 | Xiao et al. | 324/319 |

FOREIGN PATENT DOCUMENTS

| | | |
|---|---|---|
| JP | 03-018782 | 1/1991 |
| JP | 09-299351 | 11/1997 |

OTHER PUBLICATIONS

George A. Pinard, et al.; Magnet and Gradient Coil System for Low-Field EPR Imaging; 2002 Wiley Periodicals, Inc. Concepts in Magnetic Resonance Engineering; pp. 51-58; vol. 15(1).

* cited by examiner

*Primary Examiner*—Louis M Arana
(74) *Attorney, Agent, or Firm*—Antonelli, Terry, Stout & Kraus, LLP.

(57) ABSTRACT

A compact, lightweight, and easy-to-use ESR-CT apparatus including a magnetic field leak line (5-G line) which is capable of imaging a small animal, such as a mouse, within 15 minutes, and of observing a desired region with a spatial resolution of 1 mm or less. A permanent magnet system is introduced of the apparatus includes pole pieces having a predetermined area which are opposed to each other through a measured space, yokes combined with the pole pieces, and a permanent magnet inserted in series so that at least one magnetic pole plane intersects perpendicularly to the closed magnetic circuit for magnetic coupling with the yokes. This makes it possible to locate a gradient coil system and a field scanning coil system sufficiently apart from end faces of the pole pieces, and to downsize the field scanning coil system so that the gradient field system is movable.

17 Claims, 11 Drawing Sheets

MAGNETIC FIELD DISTRIBUTION
FOR MEASURED SPACE (EXPERIMENTAL)

APPARATUS FOR ELECTRON SPIN RESONANCE CT

CLAIM OF PRIORITY

The present invention claims priority from Japanese application JP 2006-245597 filed on Sep. 11, 2006, the content of which is hereby incorporated by reference on to this application.

BACKGROUND OF THE INVENTION

The present invention relates to a magnetic field resonance imaging apparatus, and more particularly to a magnetic field resonance imaging apparatus suitable for high-speed imaging with high resolution.

With the decrease in candidate compounds for new medicines and the increase in attention to security for the human body, the cost of new drug development by pharmaceutical companies is dramatically increasing and accordingly the number of mice used for animal experiment is also remarkably increasing. The demand for decreasing the number of small animals used for experiment in the stage of animal experiment called pre-clinic is increasing from the viewpoint of cost reduction and small animal protection. Furthermore, there is an increasing demand for a diagnostic imaging tool which allows observation and experiment with the living body as a support tool for medications development which makes it possible to observe drug effect in the living body and examine effect of a drug designed by a specific part-targeting of the living body.

In connection with conventional technologies concerning the above, such as MRI (nuclear magnetic resonance imaging) using nuclear magnetic resonance (NMR) and ESR-CT (electron spin resonance imaging) using electron spin resonance (ESR), commercial apparatuses targeting small animals have already been put on the market. CW (continuous wave)-based ESR-CT is used in many cases while pulse-based ESR-CT is studied in rare cases. With a magnetic resonance imaging system aiming at imaging in the living body, the frequency is limited to a radio frequency of 1.2 GHz or lower to image a deep portion of the living body even in case of a small animal, because of attenuated irradiation electromagnetic wave caused by water in the living body.

Irrespective of MRI or ESR-CT, with magnetic resonance CT, a gradient coil system for specifying a location where a signal is generated is placed in a uniform static magnetic field. Then a gradient field strength is varied for imaging. In this case, magnetic resonance CT is characterized in that the origin of coordinates of a shot image agrees with the origin of coordinates of the gradient coil system. In the case of MRI, since the hydrogen atomic nucleus (proton) is subjected to imaging, morphological images of the living body are obtained. Therefore, there has been a problem of finding out a target image from a huge amount of morphological images in order to discover an affected region. In the case of ESR-CT, since a radical contrast agent specific to ESR is applied to a small animal to image a distribution, it is difficult to obtain morphological images. However, since the contrast agent distribution is immediately imaged, ESR-CT is characterized in that finding out an affected region is easy if it is linked with the contrast agent distribution.

Hereinafter, the present invention is applied to ESR-CT technology using electron spin resonance (ESR) and therefore will be disclosed taking ESR-CT into consideration.

ESR-CT comprises a static magnetic field generator for generating a uniform magnetic space as a space for measuring a small animal (a measured space); a gradient coil system for imaging; an RF probe for radio wave transmission and reception; and a console system for controlling these elements. In the case of the CW method, a field scanning coil system is additionally provided. In the actual CW method, a field modulation coil system is additionally provided to apply AC field modulation for superposition on field scanning. However, the field modulation coil system is not related to the present invention and therefore will be omitted in the following disclosure.

When performing diagnostic imaging of the living body of an experimental small animal under anesthesia to alleviate the burden to the living body, the imaging time is limited to about 15 minutes because of the physical strength of the small animal. In the case of imaging under weak anesthesia or without anesthesia, it is desirable to complete imaging within a shorter period of time because there is a risk that the animal wriggles the body. When observing the living body of a small animal with time, it is valuable to make the imaging time as short as possible. The reduction in the imaging time is a pressing issue also from the viewpoint of efficient diagnostic imaging. With conventional MRI or ESR-CT, there has not been much demand for performing diagnostic imaging of the living body of an experimental small animal, and therefore the problem of the long imaging time has not been emerged as a common problem.

As a "molecule imaging" tool which visualizes biological reaction in the living body by imaging, on the other hand, the clearness of image, i.e., high spatial resolution is required. Although it is best to image the living body with high speed and high resolution, actual needs do not necessarily require high speed and high resolution. For example, there are two different objects of visualization of biological reaction. One is to survey the whole living body of a small animal, etc., and the other is to observe minutely a target portion. It is desirable that both objects of imaging be accomplished with an identical single apparatus. When surveying the whole living body, high-speed imaging is required even if the spatial resolution is given up to some extent. When observing minutely a target portion, there are two different cases. One is observing a predetermined target portion (for example, when a known lesion in the kidney is observed or when the function of the kidney is observed), and the other is observing a lesion discovered from images shot by surveying the whole living body (by means of a kind of an optical microscope or zoom-in function of a digital camera).

Conventional ESR-CT apparatuses using an electromagnet as a static magnetic field generator have the following three drawbacks for the above-mentioned demands, disturbing realization of the object of the present invention, i.e., high-speed imaging and high spatial resolution.

(1) High-speed switching of gradient field cannot be performed.

(2) High-speed field scanning cannot be performed.

(3) It is difficult to image an intentionally targeted region (desired portion) with a high spatial resolution of 1 mm or less.

The reason for (1), "High-speed switching of gradient field cannot be performed" will be explained below.

The gap between the pole pieces for forming a measured space (a region subjected to imaging, such as a mouse) is small. Therefore, when installing a gradient coil system, gradient field coils will be arranged next to the yokes immediately near the pole pieces. As a result, high-speed switching of gradient field generates an eddy current in the yokes, resulting in distortions and artifacts in the image. Therefore, high-speed switching cannot actually be realized. The eddy current generated in the yokes increases with decreasing distance between the gradient field coils and the yokes and increasing switching speed of the gradient field.

In the case of ESR, relaxation time T1 which determines an upper limit of high-speed switching of gradient field strength is as short as 10 μs at maximum, and therefore it is expected that the imaging speed be increased taking advantage of this short relaxation time. Although it is desirable to set an ultrashort switching time of gradient field strength to 30 to 50 μs (equivalent to a frequency of 20 to 33.3 kHz), it has not been realized for the above-mentioned reason.

The reason for (2), "High-speed field scanning cannot be performed" will be explained below.

(i) With conventional commercial ESR-CT, a leak magnetic field is confined in the yokes to reduce a magnetic field leak line (5-G line), and an electromagnet structure with yokes is employed to improve the current magnetic field efficiency. When the magnetic field is confined in the yokes, the flux density per unit sectional area of a magnetic circuit increases, preventing time change of a coil current and disturbing high-speed field scanning. This is attributable to an increase in the effective inductance of a coil. As a result, it has taken a very long time for imaging.

(ii) If the gap between the pole pieces for forming a measured space (a region subjected to imaging, such as a mouse) is further increased, there is no other choice to enlarge the area of opposed surfaces of the pole pieces in order to guarantee the magnetic field homogeneity. With the electromagnet with yokes, therefore, the coil diameter is increased resulting in a larger yoke structure. Then, the effective inductance of the coil increases, making it further difficult to perform high-speed field scanning and resulting in an increased weight.

For above-mentioned (1) and (2), a study on an air-core electromagnet without yokes has been started with a view to improvement of commercial ESR-CT with an electromagnet with yokes (G. A. Rinard, et al.: Magnetic Resonance Engineering, Vol. 15, pages 51-58, 2002). In this example, the resonance magnetic field homogeneity of a measured space (a region subjected to imaging, such as a mouse) is achieved by an air-core coil having a resonance magnetic field strength of 90 G (equivalent to a frequency of 250 MHz), and therefore the following problems arise:

(A) The use of a coil having a large diameter (for example, 800 mm) is necessary. Since it is necessary to draw a large current (10 to 20 A), the stability of the magnetic field cannot be ensured by commercial power supply.

(B) Since inductance L increases because of the enlarged coil diameter, a time constant increases close to about 100 ms (equivalent to a frequency of about 10 Hz) prolonging the time of static field scanning, although not so long as that for an electromagnet with yokes.

(C) The gross weight of the coil system including the large-diameter coil and the gradient field coils as well as the power supply system increases.

(D) The magnetic field leak line (5-G line) increases in length to 2 m, remarkably limiting the operability and installation space. In consideration of influences on electronic devices and the human body, a structure which can make the leak magnetic field line (5-G line) compact is required for commercial systems.

If the resonance magnetic field increases to about 90 G to 400 G, the coil diameter and the coil current further increase and therefore the above-mentioned problems will become more noticeable.

If the coil current is made constant, the area of the space having a uniform resonance magnetic field of a measured space (a region subjected to imaging, such as a mouse) is uniquely determined by the coil diameter. Therefore, when the resonance magnetic field is increased, there is no other choice to enlarge the coil diameter in order to ensure the same area of the space having a uniform resonance magnetic field. In this case, the time of field scanning becomes longer, the system heavier, and the magnetic field leak line (5-G line) longer.

Therefore, the present air-core coil electromagnet system is useful for demonstration but not suitable for commercial ESR-CT apparatuses.

The reason for (3), "It is difficult to image an intentionally targeted (desired portion) region with a high spatial resolution of 1 mm or less" will be explained below.

With a conventional ESR-CT apparatus, the gradient coil system and the RF probe system are fixed with respect to a region having a uniform static magnetic field. Therefore, moving operations are only translation and rotation of the subject (imaging target, such as a mouse). Only a region near a center determined by the gradient coil system can be observed with high resolution. A desired portion cannot necessarily be imaged with high resolution. To image other regions with high resolution, it was necessary to perform translation and rotation of the subject, and then arrange a desired portion near a center determined by the gradient coil system.

To be in more detail, with the conventional ESR-CT apparatus, an absorption width ΔH of the radical under measurement is as large as about 1 to 2 G (Gauss). Therefore, in order to realize a spatial resolution of 1 mm or less in terms of the ratio of an absorption width ΔH (theoretical spatial resolution) to a gradient field strength G (gradient field strength), ΔH/G, it is necessary to set the gradient field strength to 10 to 20 G/cm or more. As a result, the power to be supplied to the gradient coil system became too high, and accordingly measurement was limited by a spatial resolution of about 1 mm because of heat generation by the gradient coil system.

On the other hand, a spatial area of about 35 mm is required as a measured space (region under measurement of a small animal, such as a mouse). Therefore, in the case of a typical resonance frequency of 250 MHz (equivalent to a resonance magnetic field strength $H_0$ of 90 G) of the ESR-CT apparatus, 35 mm×10 G/cm=35 G results when the gradient field strength is 10 G/cm. Therefore, the magnetic field strength at both ends of the measured space is 72.5 G (=90−17.5) and 107.5 G (=90+17.5) respectively, resulting in a deviation of as large as ±19.4% from the resonance magnetic field. Under this condition, imaging of the entire measured space is difficult.

In this example, it was possible to perform imaging with a spatial resolution of 1 mm or less only in a small region, $H_0/(G \times Q)$ (=90 G/(10 G/cm×80)=1.125 mm), at the center of the measured space. Here, Q denotes a Q value of an RF probe, which is about 80 when a small animal is inserted.

Therefore, when imaging a large region, there is no other choice to reduce the gradient field strength to give up the spatial resolution and therefore high-resolution imaging of the entire measured space was difficult.

Furthermore, imaging can be performed through translational movement of the center of the measured space in the Z direction (a direction of the static magnetic field) by changing the current of the electromagnet. However, since translational movement in the X and Y directions is not possible, it was not possible to observe a desired portion in the measured space with high resolution.

Since a conventional ESR-CT apparatus is based on the CW method (continuous wave method) which does not practically require a limitation on the absorption width of the radical under measurement, it is necessary to make the static field strength variable in a wide range, and a permanent magnet which fixes the magnetic field is not applied except for a micro system, such as a portable ESR with high frequency in the GHz range (for example, Japanese Patent No. 2640377). Such a permanent magnet type portable ESR has been using a pair of opposed permanent magnets as a static field generator like open MRI (for example, Japanese Patent Application Laid-Open No. 9-299351). In this case, it is usual to arrange a permanent magnet having the almost same junction area as opposed area of the pair of pole pieces.

MRI using a permanent magnet, which is also referred to as open MRI, makes it possible to secure a wide open space unlike a cylindrical superconducting magnet. MRI has been said to be a human-friendly system. However, even in the case of an open MRI system, the distance between the pole pieces is short because the ratio of the human size LM along the direction of the pole pieces to the distance La between the pole pieces, LM/La, is around 0.8. Also in the case of a compact MRI system using a permanent magnet, the distance between the pole pieces is still short because the ratio of the dimensions of the subject to the distance between the pole pieces is around 0.7 to 0.9. The primary cause of the short distance between the pole pieces is that there was no other choice to place top priority on raising the magnetic resonance sensitivity by maximizing resonance magnetic field strength.

SUMMARY OF THE INVENTION

An object of the present invention is to realize a zoom-in function to image a desired portion of a small animal, such as a mouse, with a spatial resolution of 1 mm or less; and a compact, lightweight, and easy-to-use ESR-CT apparatus including a magnetic field leak line (5-G line); the apparatus being capable of performing three-dimensional imaging of a measured space of a small animal, such as a mouse, within 15 minutes; and applicable to measurement of the living body. Specifically, an object of the present invention is to realize a structure and a method which allows high-speed switching of the gradient field and high-speed field scanning, as well as a zoom-in function which can image a desired portion of a small animal, such as a mouse, with a spatial resolution of 1 mm or less.

First of all, a method of performing three-dimensional imaging within 15 minutes will be explained below.

Recognizing that the static field strength of ESR-CT for the living body is extremely small (70 to 420 G) in comparison with MRI (3000 to 30000 G) and ESR (3000 to 15000 G), the present invention applies a permanent magnet having a high residual magnetic flux density Br and a large coersive force Hc as a static field generator, and leads a magnetic flux to opposed pole pieces through yokes opposed to the magnetic pole planes of the permanent magnet having a small junction area (an area through which magnetic flux passes) to form a static magnetic field which generates a stable uniform magnetic space between the pole pieces. This makes it possible to generate a stable uniform magnetic space while solving the above-mentioned subject by sufficiently increasing the gap between the pole pieces. Specifically, in accordance with the present invention, the permanent magnet as a static magnetic field generator and the pole pieces are combined through the yokes opposed to the magnetic pole planes of the permanent magnet having a small junction area which is about 1/3 to 1/30 times as small as than the opposed areas of the pair of opposed pole pieces.

If the above-mentioned gap between the pole pieces is large enough, it becomes possible to arrange a gradient coil system sufficiently apart from the end faces of the pole pieces. Furthermore, it becomes possible to arrange in the above-mentioned space a coil system (a field scanning coil system) which scans a magnetic field which is small enough in comparison with the static field by the permanent magnet, sufficiently apart from the end faces of the pole pieces.

What is necessary to image a desired portion of the subject with a spatial resolution of 1 mm or less is to make either the gradient coil system or the RF probe system movable with respect to the region having a uniform static magnetic field. A movable range is such that the center of the system can be moved within a measured space having a uniform magnetic field (a region subjected to imaging, such as a mouse) formed by the permanent magnet. In reality, it is effective to make the gradient coil system movable while fixing the RF probe system without changing the magnitude of a measured space (a region subjected to imaging, such as a mouse) having a uniform magnetic field. On the other hand, the RF probe system can be made movable by fixing the gradient coil system; in this case, however, a necessary volume as a measured space having a uniform magnetic field is multiplied by 8 ($=2^3$) and therefore enlargement of the permanent magnet system is necessary. Specifically, each of the longitudinal length, the lateral length, and the height of the measured space is doubled.

In accordance with the present invention, the permanent magnet as a static magnetic field generator and the pole pieces are combined through the yokes combined to the magnetic pole planes of the permanent magnet having a junction area which is 1/3 to 1/30 times as small as the opposed areas of the pair of opposed pole pieces, so as to secure a wide gap between the pole pieces. This made it possible to create a static magnetic space suitable for ESR-CT for the living body, in which the residual magnetic flux density Br of the permanent magnet was decreased to 70 to 420 G (equivalent to a resonance frequency of about 200 to 1200 MHz).

On the other hand, the wide gap between the pole pieces has lead to the following advantages:

(1) The gradient field system can be installed at a distance sufficiently apart from the end faces of the pole pieces. As a result, it has become possible to acquire ESR images hardly affected by eddy current even with an ultrahigh-speed switching time of gradient field strength of 30 to 50 µs (equivalent to a frequency of 20 to 33.3 kHz).

(2) Since a field scanning coil system, having a small magnetic field approximately one-digit smaller than the static field by the permanent magnet, is arranged sufficiently apart from the end faces of the pole pieces, it has become possible that the permanent magnet is in charge of the generation of a static magnetic field $H_0$ and a small coil in the magnetic space is in charge of a time-dependent scanning field strength Hs. Since this small coil has weak magnetic interaction with the yokes immediately near the pole pieces and apart from the yokes, it is hardly affected by the eddy current and the inductance thereof can be reduced. This allowed high-speed field scanning with several kHz and remarkably reduced imaging time.

(3) The position of the RF probe system can be fixed to a predetermined position between the pole pieces, and the gradient coil system can be made movable in the measured space having a uniform magnetic field (a region subjected to imaging, such as a mouse). Accordingly, the gradient coil system can be positioned at a desired portion of the subject to align the origin of the gradient magnetic field. As a result, although the visual field decreases, it has become possible to image a desired portion of the subject with a spatial resolution of 1 mm or less by increasing the gradient field strength, even with a small apparatus. This has realized a zoom-in function in magnetic resonance imaging which makes it possible to magnify and observe a target portion.

DETAILED DESCRIPTION OF THE PREFERRED EMBODIMENTS

First of all, a basic configuration of the present invention will be explained below.

Figure 1A:
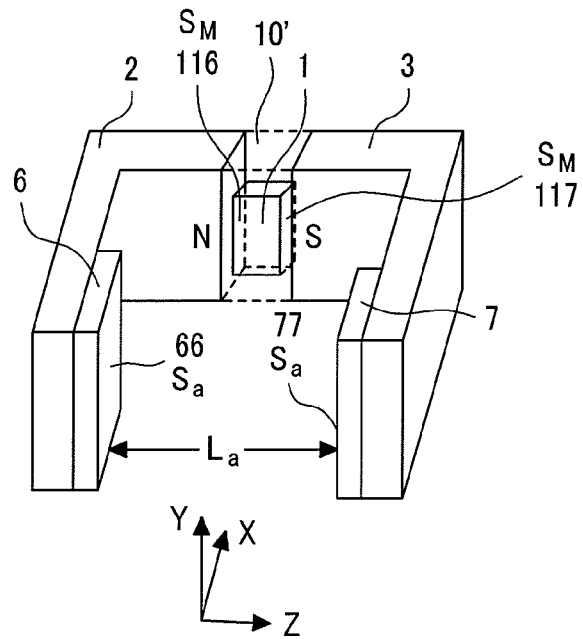
FIGS. 1A and 1B are conceptual diagrams showing a permanent magnetic system which configure a magnetic space.
Figure 1B:
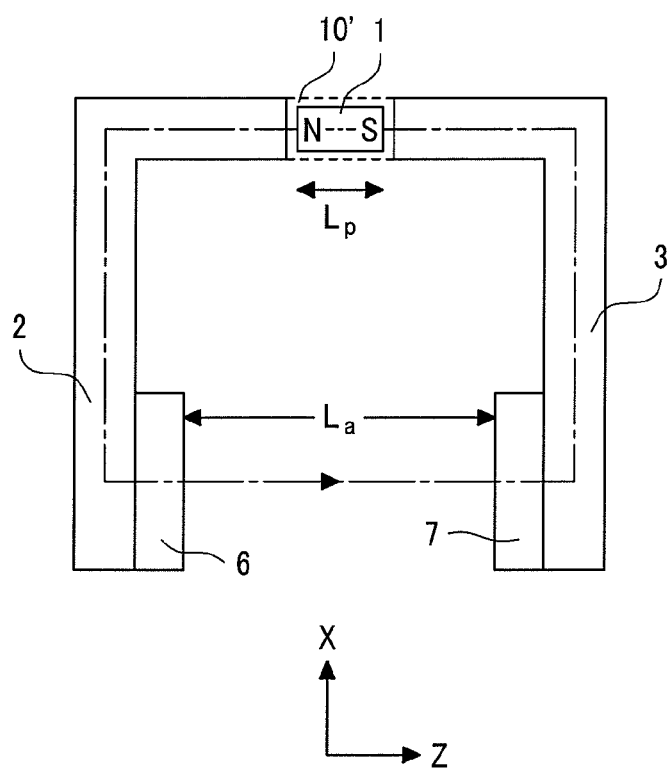

FIG. 1A is a perspective view showing a concept of a magnetic system of an ESR-CT apparatus having a permanent magnet as a static field generator and a magnetic space formed by the generator. In FIG. 1, X, Y, and Z coordinates are as shown by arrows. The static magnetic field is generated in the Z direction. FIG. 1B is a plan view showing an X-Z plane taken by cutting a permanent magnet 1. Since a flux density B and a magnetic field strength H are almost the same in air, the flux density and the magnetic field strength are the same in the magnetic space.

A reference numeral 1 is a columnar permanent magnet with magnetic pole planes formed thereon as shown by N and S. Symbol $L_p$ is a length of the permanent magnet 1. Reference numerals 2 and 3 are yokes having an L-shaped structure. Yokes 2 and 3 are larger than the height of the permanent magnet 1. A reference numeral 10' is a dummy yoke formed by a material having a low permeability. The dummy yoke 10' is arranged at the top and bottom of the permanent magnet 1 in order to conform the height of the permanent magnet 1 to that of the yokes 2 and 3. Here, in order to prevent leak of the magnetic flux of the permanent magnet 1 out of the yokes 2 and 3, it is common to design the thickness and height of the permanent magnet 1 near junctions with the yokes smaller than those of the yokes. The L-shaped yokes 2 and 3 are located so that the inner surfaces thereof are opposed to each other and one end face thereof faces to each of the end faces (magnetic pole planes) 116 and 117 of the permanent magnet 1 having a junction area $S_M$. Reference numerals 6 and 7 are opposed pole pieces which are formed on the inner surface of the other end face of the yokes 2 and 3, where $S_a$ is each of opposed areas 66 and 67 of the pole pieces. A distance between the opposed pole pieces 6 and 7 is La. Thus formed is a magnetic space including a static magnetic field using the permanent magnet 1 as a static field generator. At the center of the static magnetic space formed between the opposed pole pieces 6 and 7, a measured space (a region subjected to imaging), i.e., a space in which a subject for ESR-CT is arranged, having a uniform magnetic field and little time variation is formed. A dashed line of FIG. 1B shows a magnetic circuit loop consisting of the permanent magnet 1, the yokes 2 and 3, and the opposed pole pieces 6 and 7.

In accordance with the basic concept of the present invention, when making a magnetic space having a uniform static magnetic field for ESR-CT, a high residual magnetic flux density Br generated by the permanent magnet 1 is conducted to the opposed pole pieces 6 and 7 through the yokes 2 and 3, respectively; and then weakened by decreasing the ratio of the above-mentioned junction area $S_M$ to the area of pole pieces $S_a$, $S_M/S_a$, and increasing the spatial distance La between the pole pieces. This makes a low resonance magnetic field for ESR-CT, ensures the resonance magnetic field homogeneity of the measured space, and confines the magnetic flux from the permanent magnet in the yokes 2 and 3 to reduce the magnetic field leak line (5-G line).

The residual magnetic flux density Br of the permanent magnet 1 will be approximately 11000 G. Specifically, the present invention uses a magnetic field strength which is 26 to 157 times larger than a target resonance magnetic field strength of 70 to 420 G (equivalent to a resonance frequency of 200 to 1200 MHz) for ESR-CT in order to stabilize the magnetic field generator. As a result, the present invention aims at weakening the magnetic field strength of the measured space (between the pole pieces 6 and 7), which crucially differs from conventional MRI and conventional ESR having concentrated on strengthening the magnetic field strength.

First of all, in order to solve the above-mentioned problem, it is important to decrease an area $S_M$ (junction area) of junction surfaces 117 and 116 of the permanent magnet 1 connected with the yokes, and enlarge an area $S_a$ of the opposed surfaces of the pole pieces 6 and 7 for the purpose of decreasing the residual magnetic flux density Br of the permanent magnet 1 in the measured space. Furthermore, in order to solve the above-mentioned problem, it is important to increase the distance La between the opposed pole pieces 6 and 7 to reduce the residual magnetic flux density Br of the permanent magnet in the measured space.

In connection with the magnetic field homogeneity, the difference between maximum and minimum values of the Z-axis field strength in the measured space is ΔHv. When a small animal, such as a mouse is subjected to ESR-CT imaging with a spatial resolution of 1 mm, an expected Z-axis magnetic field homogeneity in the measured space also depends on the absorption width ΔH of a radical contrast agent. However, it is necessary that the Z-axis magnetic field homogeneity be about one-fifth of the absorption width ΔH or less. For example, when ΔH=20 mG, ΔHv becomes about 4 mG; when ΔH=300 mG, ΔHv becomes about 60 mG. It is ideal that the permanent magnet system be designed targeting such magnetic field homogeneity that allows measurement of $\Delta H=20$ mG having the smallest absorption width as a radical for ESR. In general, however, Formula (1) is required, where L is the magnitude of the measured space, $\Delta H$min is a minimum value of the absorption width of the radical subjected to imaging and $\Delta Hv$ is a difference between the maximum and minimum values of the Z-axis field strength in the measured space.

$$\Delta H_v \leq \frac{\Delta H_{min}}{5} \qquad (1)$$

A configuration in which a high magnetic field generated by the permanent magnet 1 is conducted to the opposed pole pieces 6 and 7 through the yokes 2 and 3 to generate a magnetic field between the opposed surfaces of the opposed pole pieces 6 and 7 will be explained below in more detail.

First, a simplest ideal case will be considered, in which a total magnetic flux $\Phi$ (obtained by multiplying the residual magnetic flux density Br of the permanent magnet 1 by the sectional area $S_M$ of the junction surface between the magnetic pole of the permanent magnet 1 and the yokes) generated by the permanent magnet 1 is conducted to the surfaces of the pole pieces 6 and 7 through the yokes 2 and 3. In FIG. 1A, a reference numeral 117 (or 116) is a magnetic pole plane of the permanent magnet 1, which is also the junction surface $S_M$. In this case, a Z-axis magnetic field $H_G$ as represented by Formula (2) is generated between the opposed pole pieces 6 and 7, where $S_a$ is an area of opposed surfaces of the opposed pole pieces 6 and 7.

$$\mu_0 \cdot H_G = B_r \cdot \frac{S_M}{S_a} \qquad (2)$$

Where $\mu_0$ is the permeability in vacuum.

Energy $U_G$ of the magnetic field accumulated in the magnetic space between the opposed pole pieces 6 and 7 is represented by Formula (3), where $L_a$ is a distance between the opposed pole pieces 6 and 7.

$$U_G = S_a \cdot L_a \cdot \frac{H_G^2}{2} \qquad (3)$$

The permanent magnet itself is characterized by the maximum energy product $(B \cdot H)_{MAX}$, i.e., a product of the flux density in the permanent magnet and the magnetic field strength H in the permanent magnet. Therefore, it is possible to generate a necessary field strength $H_G$ by use of the permanent magnet 1 which satisfies Formula (4), where $V_M$ is a volume of the permanent magnet 1.

$$V_M \cdot (B \cdot H)_{MAX} > U_G \qquad (4)$$

It is known from Formulas (2), (3), and (4) that, to make a small field strength $H_G$ using the permanent magnet 1 having a large residual magnetic flux density Br, it is necessary to make the area $S_a$ of opposed surfaces of the opposed pole pieces 6 and 7 large enough in comparison with the sectional area $S_M$ of the junction surfaces between the permanent magnet 1 and the yokes 2 and 3 and make the distance $L_a$ between the opposed pole pieces 6 and 7 large enough in comparison with the length $L_p$ of the permanent magnet 1. On the other hand, it is possible to configure a magnetic space having a uniform magnetic field useful for ESR-CT by choosing the permanent magnet 1 having a small volume $V_M$, using a permanent magnet having a large residual magnetic flux density as a static field generator, and conducting the magnetic flux to the pole pieces having a large area of opposed surfaces and a large distance therebetween through yokes having a small sectional area.

Since Formula (2), (3), and (4) apply to an ideal case, a more practical case in which effect of the yokes 2 and 3 is also taken into account will be explained below with reference to FIG. 1B.

A magnetomotive force F is represented by Formula (5) from the Kirchhoff's Law for magnetic circuit with an approximation in which leak of the magnetic flux $\Phi$ in the magnetic circuit is ignored, where $\Phi = B \cdot S_a$, B is a flux density between the opposed pole pieces 6 and 7, $S_a$ is an area of opposed surfaces of the opposed pole pieces 6 and 7, La is a distance between the opposed surfaces of the opposed pole pieces 6 and 7, Ly is an average length of the magnetic circuit formed by the yokes 2 and 3, $S_y$ is a cross section of the magnetic circuit formed by the yokes 2 and 3, $\mu_y$ is a permeability of the yokes 2 and 3, $L_p$ is a length of the magnetic circuit of the permanent magnet 1, H is a magnetic field strength of the permanent magnet 1, and $\Phi$ is a total magnetic flux generated by the permanent magnet 1.

$$\begin{aligned} F &= H \cdot L_p + \frac{\Phi \cdot L_a}{\mu_0 \cdot S_a} + \frac{\Phi \cdot L_y}{\mu_y \cdot S_y} \\ &= H \cdot L_p + \frac{B \cdot L_a}{\mu_0} + \frac{B \cdot S_a \cdot L_y}{\mu_y \cdot S_y} \end{aligned} \qquad (5)$$

Since the magnetomotive force F applied from outside is zero, substitution of F=0 gives Formula (6).

$$\frac{H}{B} = -\frac{L_a + \frac{\mu_0 \cdot S_a \cdot L_y}{\mu_y \cdot S_y}}{\mu_0 \cdot L_p} \qquad (6)$$

Figure 2:
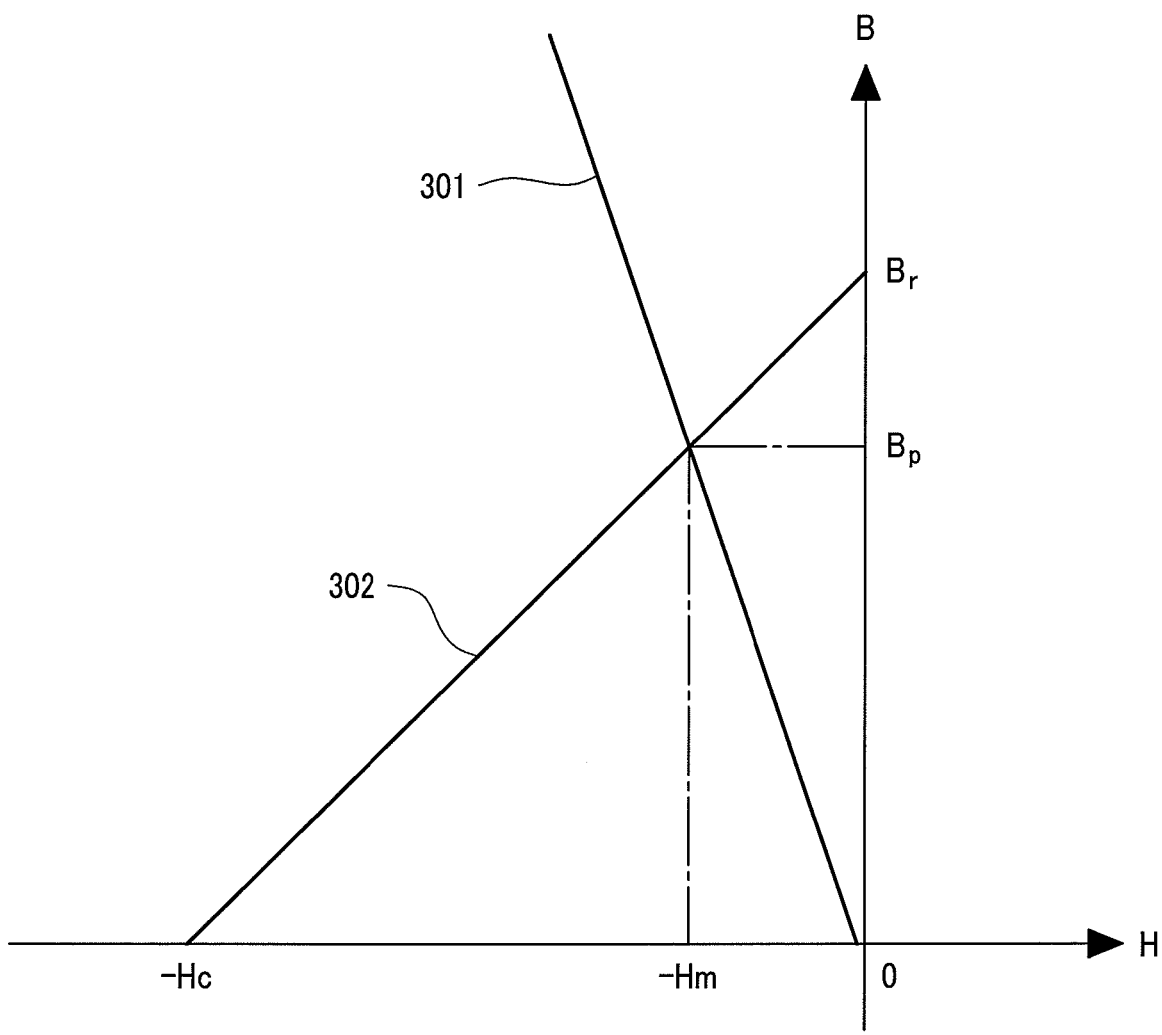
FIG. 2 is a graph for determining a magnetic field strength of a measured space.

On the other hand, a relation between the residual magnetic flux density $B_r$ and the coercive force $H_c$ of the permanent magnet 1 is shown by a demagnetization curve of the permanent magnet shown in FIG. 2. A reference numeral 301 denotes a relation between the flux density B and the magnetic field strength H in a magnetic circuit loop formed by the permanent magnet 1, and a reference numeral 302 denotes the demagnetization curve of the permanent magnet 1. From Formula (6) and a field strength $-H_m$ and a flux density $B_p$ at an intersection of the characteristic curve 301 and the demagnetization curve 302 shown in FIG. 2, a flux density B of the measured space between the opposed pole pieces 6 and 7 can be obtained as $B=B_p$ and represented by Formula (7).

$$B_p = \frac{\mu_0 \cdot H_c \cdot L_p}{\frac{\mu_0 \cdot H_c}{B_r} \cdot L_p + L_a + \frac{\mu_0 \cdot S_a}{\mu_y \cdot S_y} \cdot L_y} \qquad (7)$$

As represented by Formula (7), in order to decrease the flux density $B_p$ of the measured space, it is effective to decrease the length $L_p$ of the permanent magnet 1 and increase the gap $L_a$ between the opposed pole pieces so that the numerator of Formula (7) may decrease. If $L_a$ is large, this makes it possible to increase the magnitude of a measured space (a region subjected to imaging, such as a mouse). In order to decrease the flux density $B_p$ of the measured space, it is also effective to enlarge the area $S_a$ of opposed surfaces of the opposed pole pieces 6 and 7 in comparison with the sectional area $S_y$ of the magnetic circuit at the portions of the yokes 2 and 3.

Specifically, a structure in which the permanent magnet 1 of the present invention is used as a static field generator and a magnetic flux generated by the generator is conducted between the opposed pole pieces 6 and 7 through the yokes 2 and 3 to form a static magnetic field is essentially useful for a measured space (a region subjected to imaging), i.e., a space in which a subject for ESR-CT is arranged for a static field region formed. The length $L_y$ of the yokes, and the shape and magnitude of the sectional area $S_y$ through which magnetic flux passes and the area $S_a$ of opposed surfaces of the opposed pole pieces are determined by the magnetic field strength $B_p$ determined by a requirement from a desired ESR resonance magnetic field strength, and the magnitude of a required measured space (a region subjected to imaging, such as a mouse). However, as represented by Formula (7), the above-mentioned dimensions can have a high degree of freedom in accordance with the present invention. Details on this point will be mentioned later.

The area $S_M$ of the junction surface 117 (or 116) between the permanent magnet 1 and the yoke 3 (or 2) does not appear directly in Formula (7) because this is an approximate solution by a one-dimensional magnetic circuit in the X-Z plane taken by cutting the permanent magnet 1 of the permanent magnet system of FIG. 1A. A first embodiment discloses that the area $S_M$ of the junction surface 117 (or 116) contributes through Formula (2) to the reduction in the residual magnetic flux density $B_r$ of the permanent magnet. Of course, a system of the first embodiment has a nonlinear relation between the flux density and the magnetic field strength and therefore the confirmation by computer simulation is required for strict design. However, basic design can be started from Formulas (2) to (7).

Figure 3:
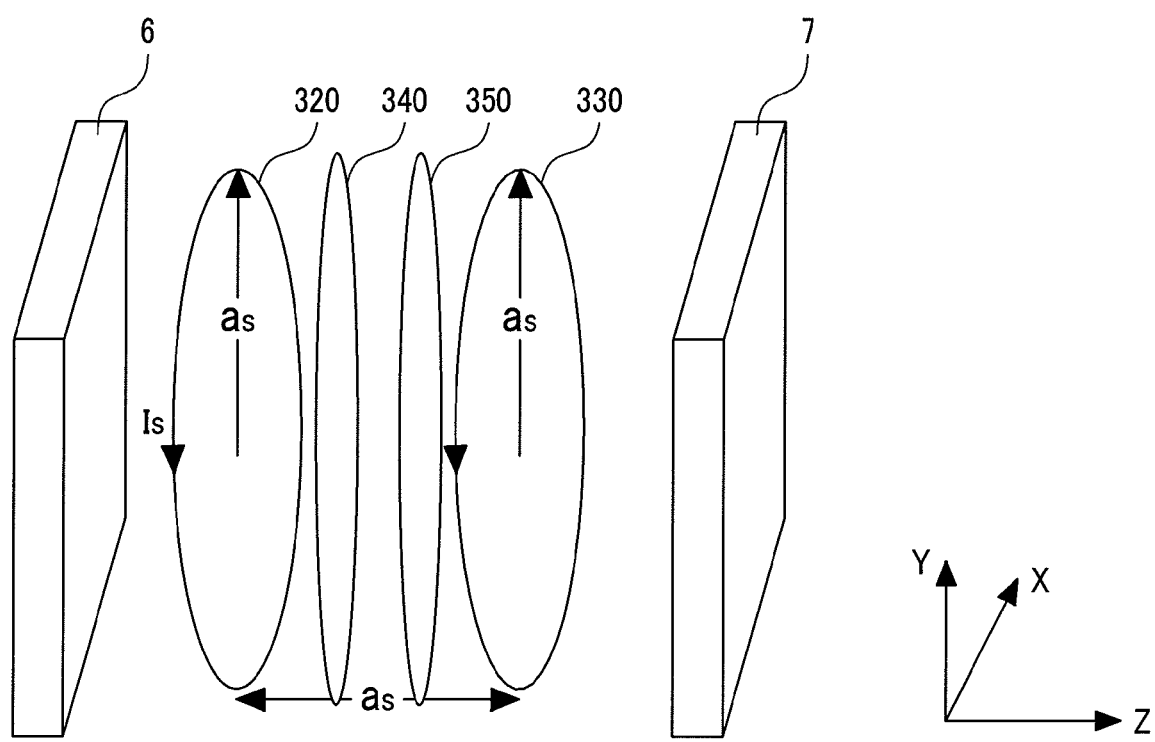
FIG. 3 is a diagram showing arrangement of gradient field coils and field scanning coils in a magnetic space.

FIG. 3 illustrates a coil system between the pole pieces 6 and 7. Reference numerals 340 and 350 denote a X, Y, Z gradient coil system; and reference numerals 320 and 330 denote Helmholtz coils forming a pair of field scanning coils. The gradient coil system and the field scanning coils are located sufficiently apart from the pole pieces 6 and 7.

Therefore, even if ultrahigh-speed switching of the gradient field is performed with a switching speed of 30 to 50 μs (equivalent to a frequency of 20 to 33.3 kHz) which is approximately one-digit faster than that of MRI, etc., ESR images can be obtained almost without occurrence of eddy current in the pole pieces 6 and 7 and respective neighboring yokes 2 and 3. CW-based ESR-CT performs imaging by superposing a scanning magnetic field on the static field. The present invention provides a system configuration which gives a magnetic space capable of including a sufficiently large measured space (a region subjected to imaging) by use of a permanent magnet as a static field generator, and allows ultrahigh-speed switching of gradient field strength by installing a compact field scanning coil system necessary for imaging in the magnetic space.

The Helmholtz coils provided as a field scanning coil system for imaging of a subject in the magnetic space formed between the opposed pole pieces 6 and 7 will be explained below based on a general theory of Helmholtz coil (for example, Basics and Clinical of NMR Medicine (published by Maruzen on Jan. 20, 1984)). A current flowing in a pair of Helmholtz coils 320 and 330 is $I_s$, a radius of each coil is as, and a distance between the coils is the same as the radius of each coil ($a_s$). X, Y, Z coordinates are established by setting the center axis of the pair of Helmholtz coils 320 and 330 as the z axis and a point at the middle of the pair of Helmholtz coils 320 and 330 as an origin. Then, the magnetic field strength H on the z axis will be considered below. As shown by Formula (8), the magnetic field strength H is represented by a sum of or a difference between a constant part $H_s$ having no relation with the Z-axis position as represented by Formula (9) and a quartic term $\Delta Hs$ as represented by Formula (10).

$$H = H_s \pm \Delta H_s \tag{8}$$

$$H_s = (0.8)^{1.5} \cdot \frac{I_s}{a_s} \tag{9}$$

$$\Delta H_s = \gamma_4 \cdot H_s \cdot \left(\frac{L}{2} \cdot a_s\right)^4 \tag{10}$$

Where $\gamma_4$ is −18.432 which is a constant having no relation with the radius of each coil, the current $I_s$ flowing in the pair of Helmholtz coils 320 and 330, and the magnitude of the measured space.

In accordance with the present invention, the magnetic field strength $H_s$ generated by the pair of Helmholtz coils 320 and 330 which are field scanning coils is at least one-digit smaller than a magnetic field $H_0$ generated between the opposed surfaces of the opposed pole pieces 6 and 7 using the permanent magnet 1 as a static field generator. Furthermore, since it is not necessary to generate the scanning field strength over the entire magnetic space and what is necessary is to cover the measured space, the radius of each coil (as) can be reduced. Accordingly, it becomes possible to reduce the inductance of each coil, remarkably reduce the current Is to flow, and locate the pair of Helmholtz coils 320 and 330 sufficiently apart from the opposed pole pieces 6 and 7, allowing configuration of a field scanning coil system capable of high-speed response with low power consumption.

Even with a conventional air-core electromagnet system, although it is possible to form a coil system for forming a static field separately from a field scanning coil system, it is necessary to align the direction in which a magnetic field is generated. Since the two coils interfere with each other because of mutual inductance, and high-speed scanning of the scanning field will affect the static field. In accordance with the present invention, since a static magnetic field is formed by a permanent magnet, the mutual inductance is very small, and the scanning coil system is located sufficiently apart from end faces of the pole pieces, and there is also little influence of eddy current allowing high-speed scanning with a switching speed of 200 to 500 μs (equivalent to a frequency of 2 to 5 kHz).

Specifically, taking into consideration a case where a main field strength $H_0$ is given by means of Helmholtz coils, a specific advantage of a small coil is shown below.

As represented by Formula (11), it is necessary to design a coil system so that the absolute value of the variable part of the magnetic field strength, $\Delta H_s$, by current control of the Helmholtz coil satisfies the right-hand side of Formula (1).

$$|\Delta H_s| \leq \frac{\Delta H_{min}}{5} \quad (11)$$

When a radius of the coil giving $H_0$ is a, a current to flow is $I_0$, the variable part of the magnetic field strength, $\Delta H_s$, represented by Formula (10) gives the same variable range of the magnetic field, $\Delta H_v$, represented by Formula (1), and the same variable range is required for large and small coils, Formulas (12) and (13) are given by Formulas (9) and (10).

$$\frac{a_s}{a} = \left(\frac{H_s}{H_0}\right)^{0.25} \quad (12)$$

$$\frac{I_s}{I_p} = \left(\frac{H_s}{H_0}\right)^{1.25} \quad (13)$$

In the case of $H_0=70$ G and $H_s=3.5$ G, for example, $a_s/a=0.47$ and $I_s/I_0=0.024$ are given, largely contributing to the decrease in size and current consumption of the coils. From Formulas (12) and (13), this effect further increases if the main field strength $H_0$ exceeds 70 G (90 to 400 G).

The same effect can be expected even when double Helmholtz coils having favorable magnetic field homogeneity are used instead of Helmholtz coils.

An imaging method and a zoom-in function will be explained below.

A gradient field vector G by gradient field coils is generally represented by Formula (14).

$$G=(G_x, G_y, G_z) \quad (4)$$

where $G_x$ is a Z-axis component of the gradient magnetic field depending on the X-axis position, $G_y$ is a Z-axis component of the gradient magnetic field depending on the Y-axis position, and $G_z$ is a Z-axis component of the gradient magnetic field depending on the Z-axis position, which are generated by the X, Y, and Z gradient field coils, respectively. When Formula (15) is satisfied using the Q value of the RF probe and the static field strength $H_0$, where G is an absolute value of vector G and L is a magnitude of the measured space, it is possible to image the distribution of a radical matter which exists in the measured space.

$$G \cdot L \leq \frac{H_0}{Q} \quad (15)$$

In this case, the theoretical spatial resolution of the radical distribution can be represented by $\Delta H/G$, where $\Delta H$ is an absorption width of the radical matter and G is a gradient field strength. Formula (16) can be derived from Formula (15).

$$\frac{\Delta H}{G} \geq \frac{\Delta H \cdot Q \cdot L}{H_0} \quad (16)$$

Figure 4A:
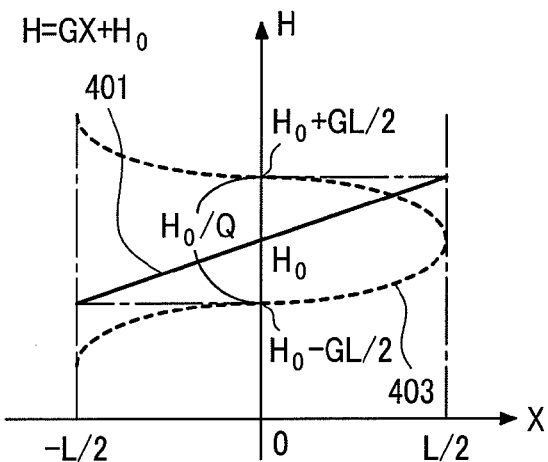
FIGS. 4A to 4C are diagrams showing arrangements of split regions of a measured space in a magnetic space.

FIG. 4A is a diagram showing variation of the magnetic field strength with respect to a position when a gradient magnetic field having a gradient field strength G is applied to the X-axis direction, where L is an X-axis magnitude of the measured space. In FIG. 4A, the horizontal axis is assigned the X coordinate and the vertical axis the magnetic field strength H, giving a relation represented by Formula (17). A line shown by a reference numeral 401 in FIG. 4A satisfies Formula (17).

$$H=GX+H_0 \quad (17)$$

A line shown by a reference numeral 403 illustrates a concept of static field dependability of resonance characteristics of the RF probe at a position X=0, when an object under measurement, such as a mouse, is inserted into the RF probe. There is a peak at a position with the magnetic field strength $H_0$, and resonance characteristics are halved when the magnetic field strength H equals $H_0 \pm H_0/(2Q)$. A region in which resonance characteristics of the RF probe can be utilized is within a range $H_0/Q$ (hereinafter referred to as half-value width $H_0/Q$) centering on the resonance point. In other words, imaging is not possible outside this range. Here, Q is a physical quantity Q value which gives the half-value width of resonance characteristics of the RF probe. With increasing Q value, resonance characteristics become sharper and the measurement region decreases. On the other hand, since a gradient magnetic field is applied to the measured space, a difference in static field by the gradient field at both ends of the measured space (X=±L/2) equals the magnitude of G·L. With a small gradient field G, Formula (15) is satisfied. In this case, the value of $H_0/Q$ is larger than G·L allowing the entire measured space to be imaged with the RF probe.

When the current in the gradient field coils is increased to increase the value of G, the equal sign of Formula (15) applies. When the current is further increased, a portion having a high gradient field strength will exceed the range of the half-value width $H_0/Q$ centering on the resonance point, and therefore the imaging region is limited to a narrow range of $H_0/(2QG)$ centering on the origin. The diagram shown in FIG. 4A applies to a case when the equal sign of Formula (15) applies.

A method of imaging the entire measured space when the gradient field strength changes as $G \cdot L \geq H_0/Q$, i.e., when the inequality sign of Formula (15) is reversed will be disclosed below. In this case, the entire measurement space is basically split into X, Y, and Z-axis directions, imaging is made for each split block. When image data of all blocks have been obtained, a total image is configured. Since the imaging time decreases with decreasing number of split blocks, it is necessary to obtain a rational minimum number of splits.

Figure 4B:
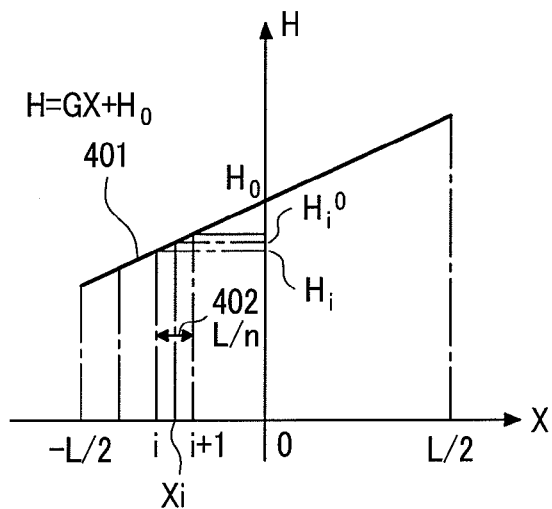

First, split of a measured space in the case of one dimension will be explained below with reference to FIG. 4B. A case when splitting a system into n regions will be considered below. The system has a linear gradient field having a gradient field strength G, i.e., a magnetic field strength of the line shown by a reference numeral 401 (FIG. 4B) in a measured space having a ±L/2 X-axis range centering on the origin. Numbers 1, 2, . . . , n are assigned to n regions from left to right. Since a length 402 of each region is L/n, when a midpoint of an i-th split region, i.e., a midpoint between positions i and i+1 is defined as Xi, Xi is represented by Formula (18) based on simple calculation. In FIG. 4B, magnetic fields at positions i and i+1 of the i-th split region are defined as H and $H_{i+1}$, respectively; and the magnetic field at position Xi as Hi0.

$$Xi = \frac{L(i-1/2)}{n} - \frac{L}{2} \quad (18)$$

Likewise, a case when the gradient field strength G is applied to the Y-axis and Z-axis directions will be considered below. When a midpoint of the j-th split region in the Y-axis direction is Yj, and the k-th split region in the Z-axis direction is Zk; Yj and Zk are represented by Formulas (19) and (20), respectively, like Formula (18).

$$Yj = \frac{L(j-1/2)}{n} - \frac{L}{2} \tag{19}$$

$$Zk = \frac{L(k-1/2)}{n} - \frac{L}{2} \tag{20}$$

When the ratio of the half-value width $H_0/Q$ of the RF probe to the gradient field strength G is now defined as $L_0$, Formula (21) is obtained.

$$L_0 = \frac{H_0}{GQ} \tag{21}$$

In the present case, $L_0$ is not larger than the magnitude L of the measured space ($L_0 \leq L$). When Formula (21) is used, the number of splits n is represented by Formula (22) in the case of one dimension.

$$n = \left[\frac{L}{L_0}\right] + 1 \tag{22}$$

However, $[L/L_0]$ is defined by Formula (23) which represents a maximum integer not exceeding $L/L_0$.

$$\left[\frac{L}{L_0}\right] = m \quad \left(m < \frac{L}{L_0} \leq m+1, m \text{ is integer}\right) \tag{23}$$

The reason why the number n of splits is determined by Formula (22) is that $L/L_0$ cannot be an integer and therefore what is necessary is to split the space by a minimum integer not less than $L/L_0$.

Figure 4C:
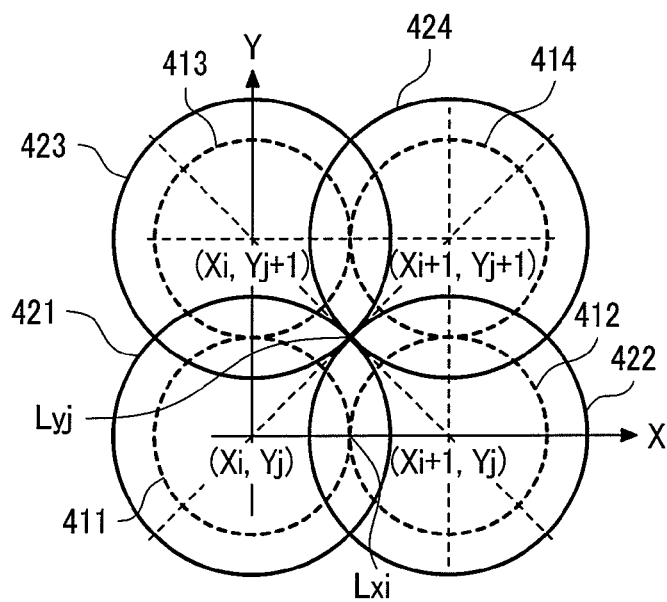

In the case of two- and three-dimensions, this problem becomes somewhat complicated. For simplicity, the same maximum gradient field strength in the X, Y, and Z directions (isotropic gradient field) is assumed. Distribution of (Xi, Yj) in the case of two dimensions is illustrated in FIG. 4C. When the magnitude L of the measured space is split into n blocks, circles in contact with each other in the X- and Y-axis directions from respective center of split are shown by dotted lines 411 to 414. Furthermore, circles in contact with each other in ±45-degree directions are shown by solid lines 421 to 424.

In the case of two dimensions, when imaging each individual split region, it is necessary that split regions be overlapped at least on areas shown by solid lines 421 to 424. In the case of two dimensions, the diameter of a circle shown by a solid line is square root of two times that of a circle shown by a dotted line and therefore the number of splits is represented by Formula (24).

$$n = \left[\frac{\sqrt{2}L}{L_0}\right] + 1 \tag{24}$$

Likewise, in the case of three dimensions, the diameter of a circle shown by a solid line is square root of three times that of a circle shown by a dotted line and therefore the number of splits is represented by Formula (25).

$$n = \left[\frac{\sqrt{3}L}{L_0}\right] + 1 \tag{25}$$

If maximum gradient field strengths differ in the X, Y, and Z directions (anisotropic gradient field), it can easily be expanded. Assuming that the maximum gradient field strengths in the X, Y, and Z directions are $G_{xmax}$, $G_{ymax}$, and $G_{zmax}$, respectively. If $L_{0x}$, $L_{0y}$, and $L_{0z}$ respectively corresponding to the X, Y, and Z directions are defined by Formula (21) with G replaced with $G_{xmax}$, $G_{ymax}$, and $G_{zmax}$, respectively, it is preferable to replace Formula (25) which determines the number of splits of space with Formula (26).

$$n = \lfloor \sqrt{(1/L_0 x)^2 + (1/L_0 y)^2 + (1/L_0 z)^2} L \rfloor + 1 \tag{26}$$

In actual measurement, since the gradient field strength G is determined before imaging, the origin of the gradient magnetic field is moved to a spatial split point in the X, Y, and Z directions determined by the above-mentioned Formula (25), Formula (18), Formula (19), and Formula (20); and then imaging is performed for each split block. Then, when image data of all blocks have been obtained, a total image is configured.

An imaging method will be explained below in more detail.

When making magnetic resonance imaging, the origin of an image agrees with the origin of the gradient magnetic field. The origin of the gradient magnetic field refers to a point at which a magnetic field strength equivalent to static field strength $H_0$ is given when a gradient field vector G is applied in the measured space having a uniform static magnetic field (with a Z-axis static field strength of $H_0$). In other words, the origin of the gradient magnetic field refers to a point at which the effective gradient field strength is zero. Usually, a gradient coil system has geometrical symmetry around the Z axis and in many cases the Z coordinate is designed within a pair of gradient field coils. Coordinate axes of a measured space having a uniform field are also designed in agreement with the geometric center of a pair of pole pieces in many cases.

Thus, when the gradient field strength is large and the inequality sign of Formula (15) is reversed, only a narrow range $H_0/(2QG)$ from the center of the gradient field is subjected to imaging. In order to image a radical distribution space in regions out of the range, it is effective to move the origin of the gradient field strength to the regional center of the subject subjected to imaging.

Figure 5A:
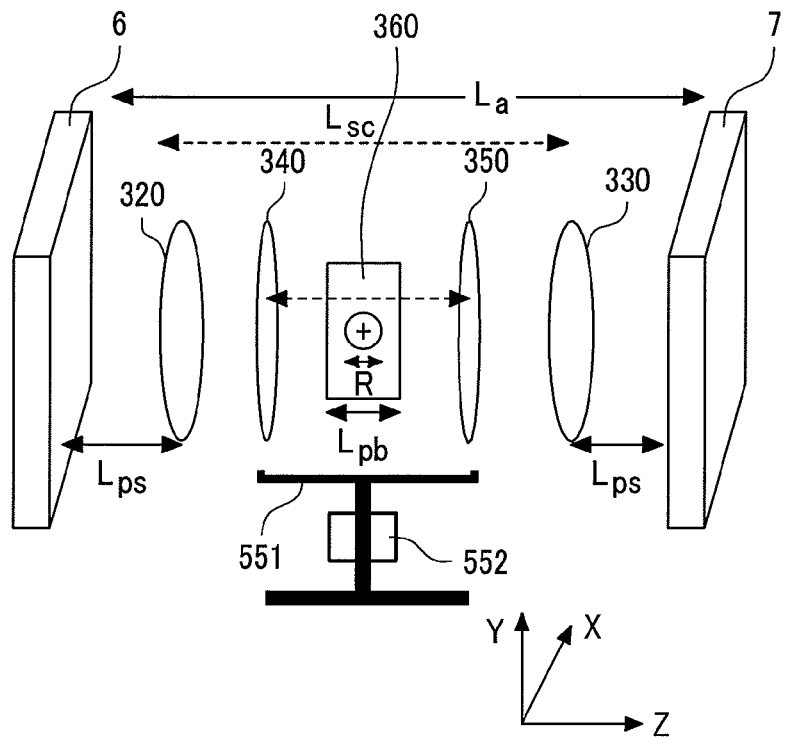
FIGS. 5A and 5B are diagrams illustrating a method of moving a gradient coil system in a magnetic space.

As shown in FIG. 5A, a pair of field scanning coils 320 and 330 and an RF probe system 360 are fixed in a region La between the pole pieces 6 and 7. Here, a method of fixing the pair of coils and the RF probe system between the pole pieces 6 and 7 will not be explained because a conventional method is applied. On the other hand, a pair of X, Y, Z gradient field coils 340 and 350 is retained by use of a non-magnetic instrument 551. It becomes possible to image a region under measurement with a high spatial resolution of 1 mm or less by installing an apparatus 552 which accurately moves this non-magnetic instrument 551 in the X, Y, and Y directions in a uniform magnetic space in a region La between the pole pieces 6 and 7, in which a subject under measurement is located centering on the origin position of the gradient field. A round space on an RF probe system 360 denotes a location of a sample under measurement (living body, such as a mouse or a rat), and a cross mark denotes a center of the Z-axis static field (an origin of the measured space).

When making the gradient coil system movable, it is necessary to accurately align the center of the static field with the origin of the gradient field in advance. To accomplish this object, the center of the static field known from the design of the permanent magnet is aligned with the origin of the gradient field strength known from the design of the gradient coil system in advance. These origins can be aligned by use of the geometrical form of the permanent magnet and the gradient coil system. Then, both origins can be corrected by measuring ESR resonance of a material having a small absorption width of 20 mG to allow monitoring. Usually, the above-mentioned origins can be aligned with an accuracy of 1 mm or less.

Figure 5B:
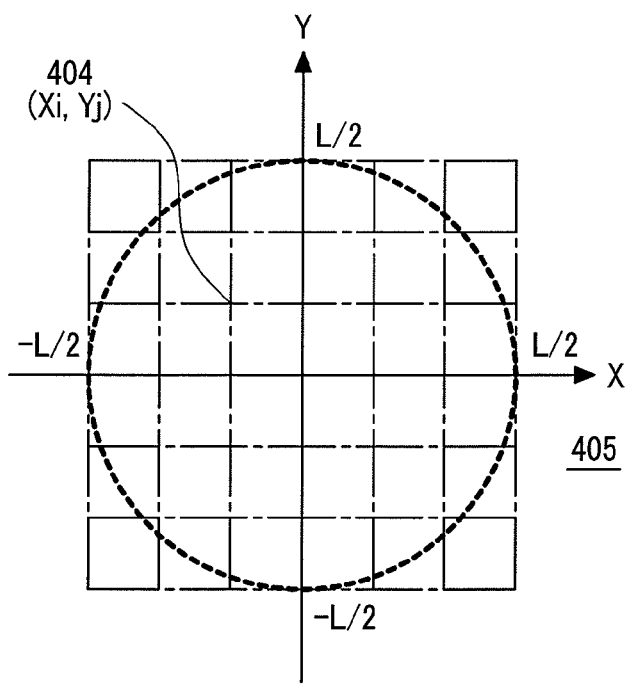

In the case of the three dimensions, a z=0 plane in a spherical measured space is shown in FIG. 5B for a case of the same maximum gradient field strength G in the X, Y, and Z directions. In this case, Formula (27) shows the gradient field vector G formed by the gradient field coil.

$$G=\sqrt{(G_x^2+G_y^2+G_z^2)} \qquad (27)$$

In the case of spherical symmetry with a constant gradient field vector G and an identical range setting of Gx, Gy, and Gz, the entire measured space can be imaged by moving the origin of the gradient field strength to a spatial split point (Xi, Yj, Zk) determined by Formula (25) and Formulas (18) to (20) and then performing imaging at all split points (Xi, Yj, Zk).

A measured space region 405 on the Z=0 plane and a split point 404 (Xi, Yj) (on the Z=0 plane) are shown in FIG. 5B. A high-resolution image over the entire measured space can be combined by moving the origin of the gradient field strength to a spatial split point (Xi, Yj, Zk) in the measured space region 405 and then sequentially acquiring imaging data.

On the other hand, if a region to be observed with high resolution is predetermined, high-resolution imaging becomes possible by aligning the origin of the gradient field coil with an estimated center of a region of interest and then performing imaging while changing the gradient field strength around the region.

A method of realizing a spatial resolution of 1 mm or less by zooming in a desired location according to the present invention has been disclosed. Specific conditions imposed to realize the present invention will be explained below with reference to FIG. 5A. The round space on the RF probe system 360 denotes a location where a sample under measurement (living body, such as a mouse and a rat), and a cross mark denotes a center (origin of the measured space) of the Z-axis static field. Transmit and receive coils are formed in the RF probe system. Specifically, in a space region in which the magnetic field homogeneity of Formula (1) is guaranteed, arrangements of the coil systems formed between the pole pieces 6 and 7 are as shown in FIG. 5A, where $L_a$ is a distance between the pole pieces 6 and 7, R is an inner diameter of the receive coil of the RF probe system, $L_{pb}$ is a width of the RF probe system 360, $L_{GC}$ is an interval between the opposed gradient field coils 340 and 350, $L_{SC}$ is an interval between the opposed field scanning coils 320 and 330, and $L_{PS}$ is a distance between the field scanning coil system and the pole pieces. Since the gradient coil system shown in FIG. 5A includes gradient field coils mounted on a substrate, the substrate has a mount thickness for the coils. In this case, a distance including the interval $L_{GC}$ between the gradient field coils 340 and 350 and the mount thickness is referred to as a width of the pair of gradient field coils, $L_{GC}'$, which is distinguished from the interval $L_{GC}$. This also applies to the field scanning coil system.

In order to allow the origin of the gradient magnetic field to freely move at least in the measured space, it is essential that the interval $L_{GC}$ between the gradient field coils 340 and 350 is larger than the width $L_{pb}$ of the RF probe system 360. Specifically, it is necessary that the condition of Formula (28) be satisfied.

$$L_{GC} > R + L_{pb} \qquad (28)$$

In order to move the origin of the gradient coil system to a desired location in the measured space and then perform zoom-in imaging, it is sufficient to satisfy the condition of Formula (28) which guarantees that the origin of the gradient field coil system can freely move in a space defined by the inner diameter R of the receive coil of the RF probe system.

Furthermore, in order to make the pair of gradient field coils 340 and 350 movable, the sum of the interval $L_{SC}$ between the opposed field scanning coils 320 and 330 and the width $L_{pb}$ of the RF probe system 360 is larger than the sum of the interval $L_{GC}$ between the opposed gradient field coils 340 and 350 and the width $L_{GC}'$ of the gradient field coils 340 and 350. Specifically, it is necessary to satisfy the condition of Formula (29).

$$L_{SC} + L_{pb} > L_{GC} + L_{GC}' \qquad (29)$$

Formula (29) gives a condition with which the gradient coil system does not come in contact with the field scanning coil system when the origin of the gradient coil system is moved according to Formula (28).

On the other hand, in order to perform high-speed scanning of the pair of field scanning coils 320 and 330 with up to several kHz, it is necessary that the distance $L_{PS}$ between the field scanning coil system and the pole pieces be about 50 mm or more to prevent eddy current from occurring in the yokes and pole pieces. Specifically, it is necessary to satisfy the condition of Formula (30).

$$L_{PS} \geq 50 \text{ mm} \qquad (30)$$

Thus, it is important that the distance La between the pole pieces 6 and 7 be at least 100 mm larger than the sum of the interval $L_{SC}$ between the opposed field scanning coils 320 and 330 and the thickness of the pair of field scanning coils (width of the field scanning coil system).

In the above specific explanation, the CW method (continuous wave method) ESR-CT was taken into consideration. In the case of the pulse-based ESR-CT, the field scanning coil system is not necessary and therefore conditions of Formulas (29) and (30) will be changed as follows. Formula (29) uses the distance $L_a$ between the pole pieces instead of the interval $L_{SC}$ between the opposed field scanning coils 320 and 330, and Formula (30) uses the distance $L_{Pg}$ between the gradient coil system and the pole pieces instead of the distance $L_{PS}$ between the field scanning coil system and the pole pieces.

Since the conventional ESR-CT technology is based on the CW method (continuous wave method) which does not practically require a limitation on the absorption width of the radical under measurement, even a radical having a large absorption width can be imaged although the imaging time is prolonged. The following will disclose that the limitation on the absorption width ΔH does not practically become problematic even in the present invention because the maximum value of the absorption width of a usual radical is smaller than ΔH=5.5 G.

When the maximum value of the scanning field strength which can be formed with Helmholtz coils or double Helmholtz coils formed in a permanent magnet in a magnet space is $H_s$max, the number of splits n is determined by Formula

(25) in the case of three dimension. Therefore, a limitation shown by Formula (31) is applied to $H_s$max in order for imaging in a split space.

$$H_s\max \geq \frac{\left(\frac{\sqrt{3}H_0}{Q} + \Delta H\right)}{2} \quad (31)$$

As shown in Formula (31), $H_s$max is 0.76 G ($H_0$=70 G, Q=80) or 4.5 G ($H_0$=420 G, Q=80) and, even if 5.5 G is taken as the maximum value of $\Delta H$, $H_s$max is 3.1 G ($H_0$=70 G) or 5.0 G ($H_0$=420 G). These are one-digit smaller than the static field strength $H_0$ and therefore do not disturb the object of the present invention.

On the other hand, a modulation field strength $H_{mod}$ applied to the scanning field strength is generally limited by Formula (32).

$$H_{mod} \leq \frac{\Delta H}{2} \leq H_s\max \quad (32)$$

However, $H_{mod}$ is smaller than $H_s$max and therefore does not disturb the object of the present invention.

Finally, a method of realizing a zoom-in function will be supplemented below. Although a single gradient coil system is used in the above-mentioned description of the present invention, it would be possible that a plurality of gradient coil systems is used. The gradient coil system includes a fixed gradient coil system which mainly images the entire measured space, and a movable gradient coil system having high gradient field strength which is in charge of zoom-in function and provided with a small region subjected to imaging. The fixed gradient coil system is in charge of a range described by Formula (15). Specifically, since the fixed gradient coil system is provided with a function to image the entire measured space, the linearity of the magnetic field shown by Formula (17) is guaranteed over the entire measured space, resulting in a large-sized coil system. On the other hand, the movable gradient coil system is provided with the zoom-in function to increase the spatial resolution by increasing the gradient field strength although the region subjected to imaging decreases. In this case, the movable gradient coil system is applicable to a case when the inequality sign of Formula (15) is reversed.

Figure 6:
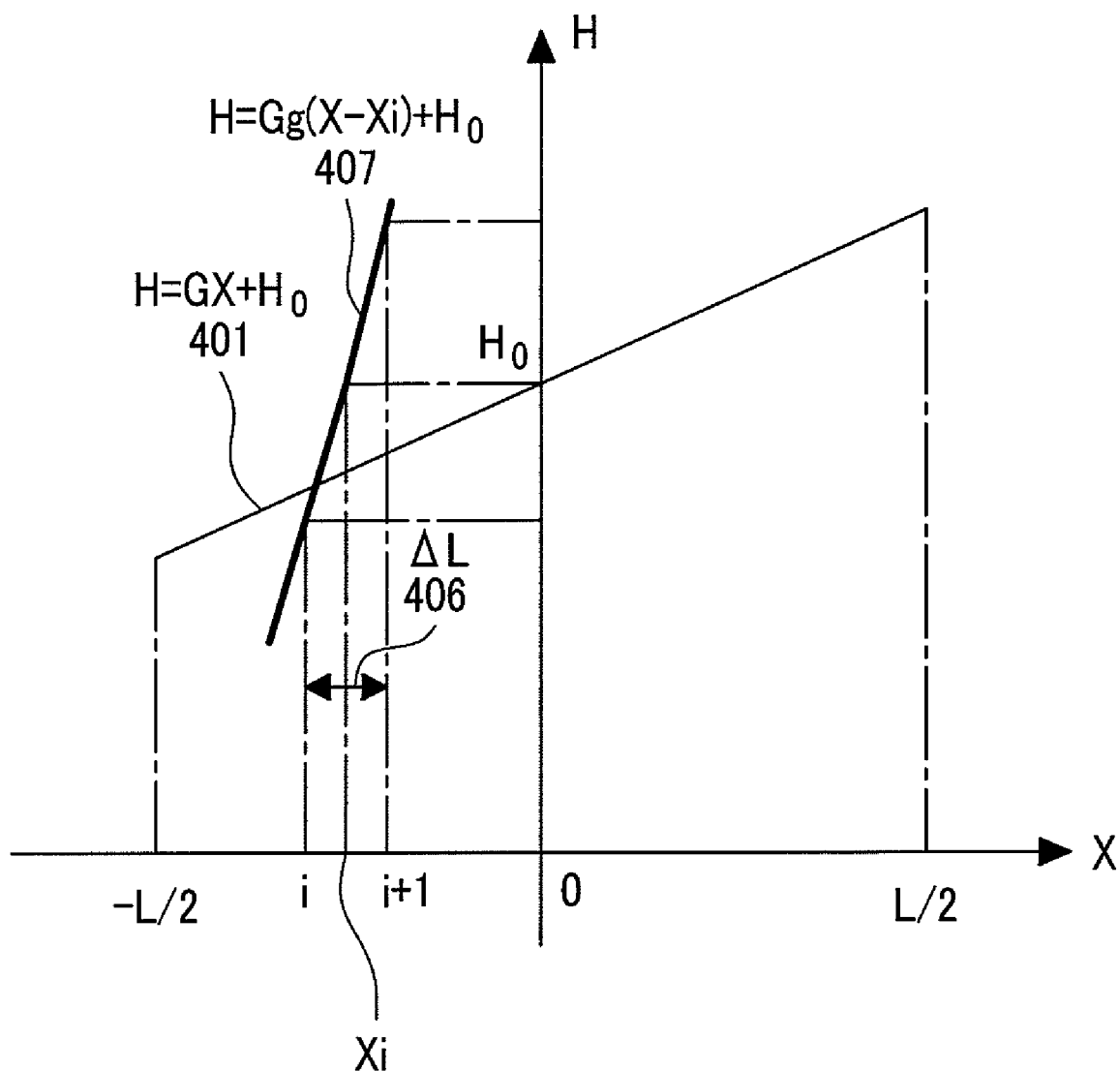
FIG. 6 is a diagram showing a zoom-in function.

A case of one dimension will be explained below with reference to FIG. 6. A gradient magnetic field 401 is applied by a fixed gradient coil system, and the entire measured space is imaged to determine a location to be zoomed in (a location to be observed with higher spatial resolution). For example, when observing a peripheral of point Xi in detail, the gradient magnetic field of the fixed gradient coil system is cut, the origin of the gradient magnetic field of the movable gradient coil system is moved to Xi to apply a stronger gradient magnetic field Gg407. In this case, a gradient magnetic field defined by Formula (33) is applied to point Xi.

$$H = Gg(X-Xi) + H_0 \quad (33)$$

At point Xi subjected to imaging according to Formula (33) depending on static magnetic field $H_0$ at point Xi, a zoom-in image of a target region 406 (FIG. 6) is obtained.

Also in the case of two and three dimensions, zoom-in images can be obtained in the same manner. For example, after imaging the measured space by use of the fixed gradient coil system, the origin of the gradient magnetic field of the movable gradient coil system is moved to a desired location (Xi, Yj, Zk), the gradient magnetic field of the fixed gradient coil system is cut, and a stronger gradient field vector (Ggx, Ggy, Ggz) is applied to image a target location (a location to be observed with higher spatial resolution).

Although the present invention has been disclosed above, it is possible to create a magnetic field having high homogeneity of magnetic field distribution and accomplish the object of the present invention by properly arranging the permanent magnet system.

First Embodiment

Figure 7A:
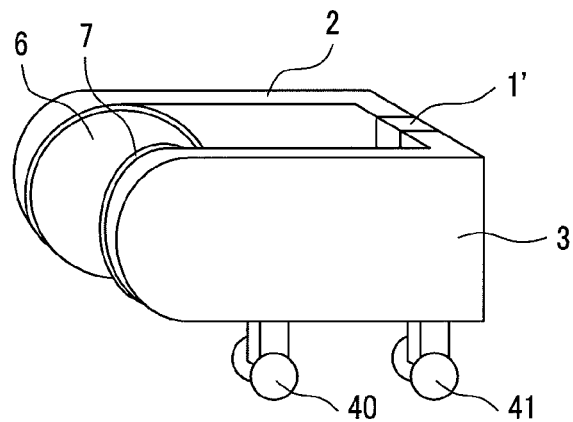
FIGS. 7A and 7B are diagrams showing another embodiment of a magnetic system by a permanent magnet which forms a magnetic space.

FIG. 7A is a perspective view showing an appearance of a magnet system for 200-MHz ESR-CT for an embodiment which uses the permanent magnet 1 (FIG. 1) of the present invention as a magnetic field generator. The same components as those in FIG. 1 are assigned the same reference numerals. With an actual structure, as is understood from the comparison with FIG. 1, the end faces of the yokes 2 and 3 are semicircle-shaped and the pole pieces 6 and 7 are disc-shaped. Reference numerals 40 and 41 are casters for transporting the magnet. A reference numeral 1' is a permanent magnet. This magnet is assigned a reference numeral different from that of the permanent magnet 1 which is embedded in the yokes as shown in FIG. 1.

In the first embodiment, a main static field strength $H_0$ caused by the permanent magnet 1 is about 71.4 G. This time, the magnitude of the measured space L (a region subjected to imaging, such as a mouse) is set to 35 mm. In order to ensure the long-term stability of the static field strength in this measured space, a Samarium Cobalt permanent magnet (having a temperature coefficient for magnetic field variation of –300 ppm/° C.) having little temperature change of the magnetic field strength at around the room temperature is used as a permanent magnet 1. In order to prevent leak of magnetic flux from the permanent magnet 10 out of the yokes 2 and 3, the width and height of the permanent magnet 1 near junctions with the yokes were designed smaller than those of the yokes.

Figure 7B:
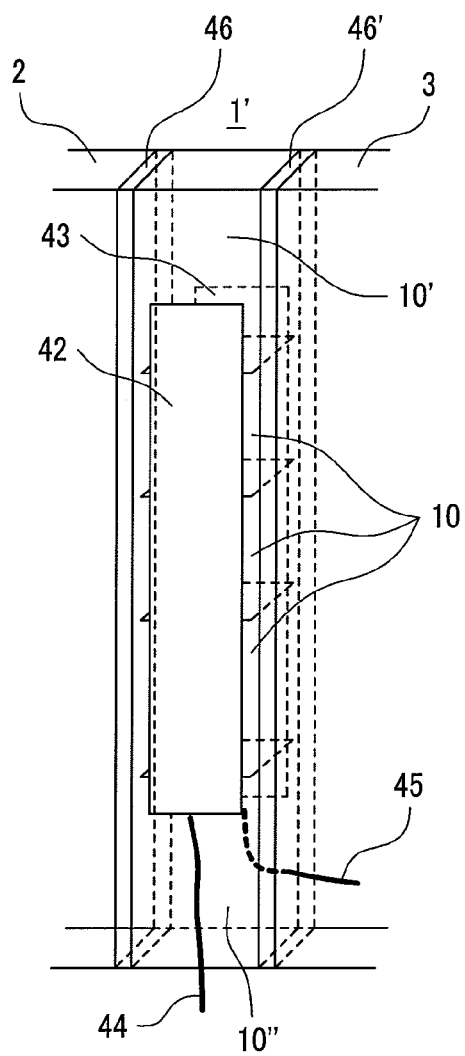

In the first embodiment, the permanent magnet 1 consists of three trisected permanent magnets 10 stacked to one another, a dummy yoke 10' at the top, and a dummy yoke 10" at the bottom, as shown in FIG. 7B. Thus, as shown in FIG. 7B, the permanent magnet 1 generally consists of several blocks of small magnets 10, which are referred to as a permanent magnet. A reference numeral 10' is a dummy yoke made of a material having a low permeability, such as aluminum. Heaters (not shown in FIG. 7B) are prepared on opposed sides of the permanent magnet 10 so that they are respectively sandwiched by the permanent magnet and the temperature sensors 42 and 43 to perform temperature detection. Reference numerals 44 and 45 schematically denote control wires of the heaters and the temperature sensors 42 and 43. A computer (not shown) for a series of temperature control is connected to the control wires 44 and 45. The temperature of the permanent magnet 10 is set to 30° C. which is several degrees higher than the room temperature, and control is made so that temperature change does not exceed ±0.01° C. Heat insulators 46 (and 46') are installed between the permanent magnet 10 and the yokes 2 (and 3).

The length Ly of the yokes is set to 1300 mm; the length Lp, thickness, and height h of the permanent magnet (FIG. 1B) are set to 50 mm, 35 mm, and 309 mm, respectively. A relative permeability $\mu/\mu_0$ of an iron yoke is about 1000. The thickness and the height h of the iron yokes 2 and 3 is set to 40 mm and 550 mm, respectively.

Figure 8A:
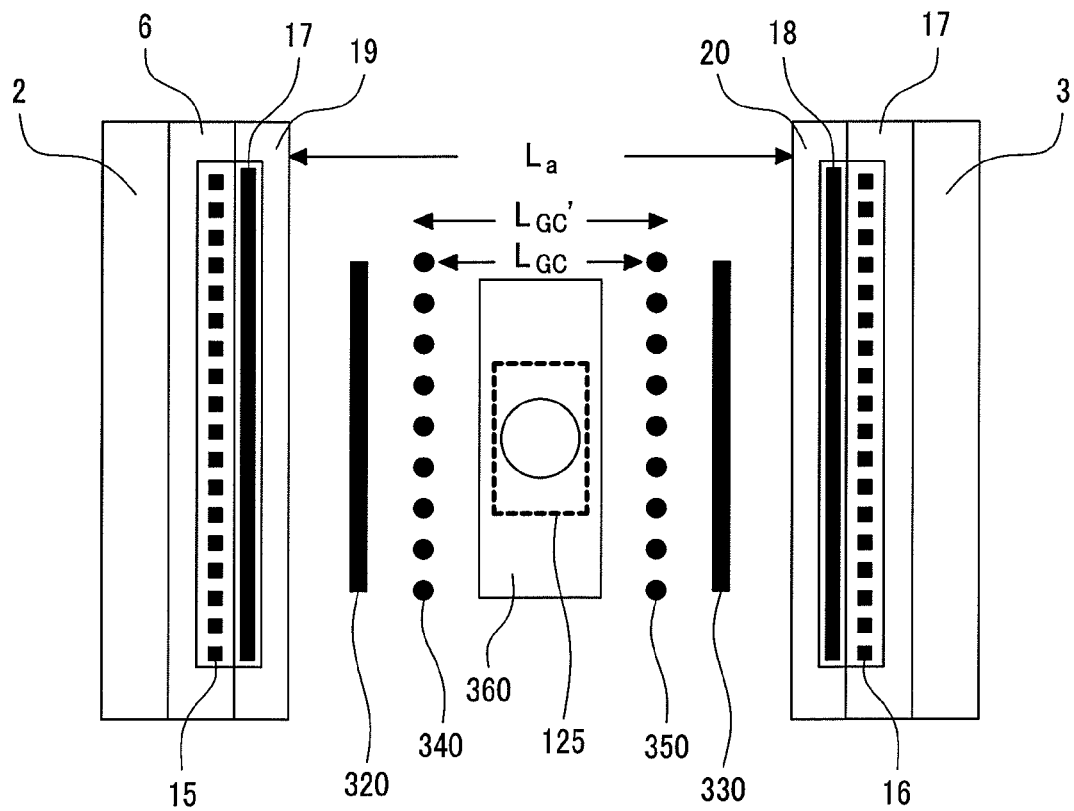
FIGS. 8A and 8B are diagrams showing arrangements of coil systems and measurement results of a magnetic field in a measured space.

FIG. 8A is a sectional view showing coil arrangements of the permanent magnet system in the magnet field, taken at the center of the pole pieces 6 and 7 and viewed along the X axis. Reference numerals 2 and 3 are yokes, reference numerals 15 and 16 are magnet shims of magnet pieces, reference numerals 17 and 18 are shim coils for minute field strength adjustment, reference numerals 19 and 20 are pole piece covers, reference numerals 340 and 350 are gradient field coils, and a reference numeral 360 is an RF probe system. Here, fixation of the coil systems and the RF probe system is not shown.

The above-mentioned system is used for a case of pulse-based ESR-CT. Reference numerals 320 and 330 are a pair of Helmholtz coils, a reference numeral 125 is a field modulation coil, which are used for CW-based ESR-CT. The field modulation coil 125 is used to apply field strength modulation of several kHz to 50 kHz on field strength scanning by the pair of Helmholtz coils 320 and 330. The present embodiment is usually used to increase the sensitivity of CW-based ESR by measuring a differential value of an ESR absorption curve. The diameter of the pole pieces 6 and 7 is 550 mm, the distance La between the pole piece covers 19 and 20 is 250 mm, the interval Lsc (magnetic space) between the opposed Helmholtz coils 320 and 330 is 140 mm, the interval $L_{GC}$ (magnetic space) between the opposed gradient field coils 340 and 350 located in Lsc is 105 mm, and the width Lpb of the RF probe system 360 is 61 mm; the width being determined by the width of an RF shield box including transmit and receive coils and the field modulation coil 125. The thickness of each of the pair of gradient field coils 340 and 350 and the pair of Helmholtz coils 320 and 330 (thickness of coils when the coils are implemented on a non-magnetic substrate) is 5 mm, the inner diameter R of the receive coil of the RF probe system 360 is 39 mm, and the width $L_{GC}'$ of the pair of gradient field coils 340 and 350 is 115 mm. These values satisfy Formula (28). The diameter of the pair of Helmholtz coils 320 and 330 is 280 mm, and the diameter of the pair of gradient field coils 340 and 350 is 300 mm. At this time, the distance Lps between the pair of Helmholtz coils 320 and 330 and the pole pieces 6 and 7 can be 50 mm or more at the time of installation, preventing eddy current from occurring in the pole pieces 6 and 7 and the yokes 2 and 3 and realizing high-speed gradient magnetic field and field scanning coils. Artifacts or blurring did not occur in ESR-CT images.

The thus-configured large distance between the pole pieces makes it possible to form the RF probe system, the gradient coil system, and the field scanning coil system between the pole pieces with lot of margins, allowing high-speed response of the gradient coil system and the field scanning coil system and accordingly high-speed imaging of a small animal, such as a mouse.

In accordance with the present invention, the magnitude L of the sample space (a magnitude of the space having a uniform magnetic field in the receive coil) is 35 mm and the distance La between the pole pieces is 250 mm, giving a ratio L/La of 0.14. Since the ratio is 0.7 to 0.9 in Patent Reference 1 and Patent Reference 2 quoted for the conventional technology, the space between the pole pieces is 5 to 6.4 times larger than that with the conventional technology.

Figure 8B:
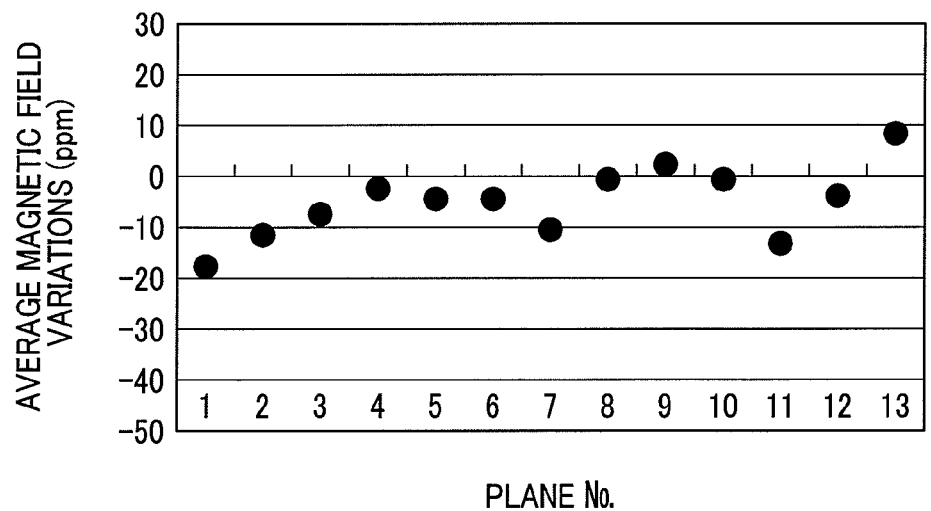

Since a Samarium Cobalt magnet has a coersive force Hc of 857 kA/m and a residual magnetic flux density Br of about 11,000 G, Formula (7) is applied to a case when the permanent magnet and the yokes arranged on both sides thereof have the same height (550 mm) in a magnetic circuit. This is equivalent to a magnetic field strength of about 1700 G using the magnetic field strength $H_G$ (hereinafter simply referred to as magnetic field strength) defined from the flux density $Bp(=\mu_0 H_G)$ on the surface of the opposed pole pieces. Formula (7) does not take into consideration the junction area between the permanent magnet and the yokes and the area of the pole pieces. If this area ratio $S_M/S_a$ of about 1/22.0 is taken into consideration, $H_G$ becomes 77.3 G from Formula (2) which is close to the target value 71.4 G. Based on this coarse estimate, specific dimensions were selected through computer simulation using a magnetic circuit with the actual shape inputted. Then, shimming was performed using magnet pieces 15 and 16 to obtain a magnetic field distribution in a measured space shown in FIG. 8B which satisfies Formula (1), where the measured space L (a region subjected to imaging, such as a mouse) is 35 mm. Here, plane No. corresponds to the split position in the measured space explained above with reference to FIG. 4B. In this case, the resonance frequency of the magnet system was 202.11816 MHz, and the resonance magnetic field strength equivalent to free electrons 72.1208 G.

At this time, the temperature dependability of the magnetic field strength at the center of the measured space was −317.7 ppm/° C. This value is very close to the temperature coefficient of the Samarium Cobalt permanent magnet 10, −300 ppm/° C. Since the temperature of the permanent magnet is controlled at 30±0.01° C., change of the magnetic field strength can remarkably be reduced even if the room temperature changes by about 23° C.±5° C. As shown by Formula (7), with a permanent magnet system in a magnetic field having a low magnetic field strength, the yokes do not largely contribute to the magnetic field strength $H_G$ and, even if there is temperature dependability of the permeability μ of the yoke material, the magnetic field strength $H_G$ does not vary largely. Therefore, even if the room temperature changes, the long-term stability of the magnetic field strength $H_G$ is guaranteed by maintaining the permanent magnet at constant temperature.

When a radical having an absorption width of 20 mG was used in a measured space L (a region subjected to imaging, such as a mouse) of 35 mm, the resonance magnetic field strength was about 72.1208 G and the Q value of the RF probe about 80 in case of mouse measurement. As shown by Formula (15), the spatial resolution in this case was about 0.78 mm. When a radical having an absorption width of 20 mG is used, the CW method is not required and high-speed imaging by pulse-based ESR-CT becomes possible. In this case, the pair of field scanning coils 320 and 330 is not used. When spin echo was integrated 4048 times, three-dimensional imaging by pulse-based ESR-CT took about 14 minutes.

Since the pair of gradient field coils 340 and 350 is apart from the yokes, no trouble occurred in high-speed response of the RF probe 360 located in the gradient field coils even if no special eddy current measures were taken other than covering with an earth shield.

Although Helmholtz coils are shown in the first embodiment, the same effect can also be expected using double Helmholtz coils.

With a radical having an absorption width ΔH of 20 to 50 mG, the relaxation time T1 and T2 are several microseconds to 10 μs allowing pulse ESR-CT, and the spin echo measurement time is 30 to 100 μs which is about four-digit faster than that for MRI. Therefore, even if the number of integrations for spin echo observation is set to several thousands, imaging-related measurement can be completed within ten-odd minutes. In particular, in the case of radical distribution with which the integration time can be one-digit order, ultrahigh-speed imaging with which imaging-related measurement is completed within several seconds. Although the number of integrations is determined by the combination of the signal intensity of the radical and the image quality, the present embodiment is much more advantageous than MRI because observation for three-dimensional imaging can be completed within ten-odd minutes even if the number of integrations is set to order of several thousands. Although the present embodiment has been explained based mainly on imaging by pulse-based ESR, it goes without saying that CW-based imaging, which is a mainstream of ESR-CT, is also possible.

Unlike MRI using a superconductivity magnet, the present apparatus requires less maintenance works, allowing it to be installed in a facility for experimental animals (for example, a laboratory with strict biotechnological classification) having strict controlled areas.

Second Embodiment

Figure 9A:
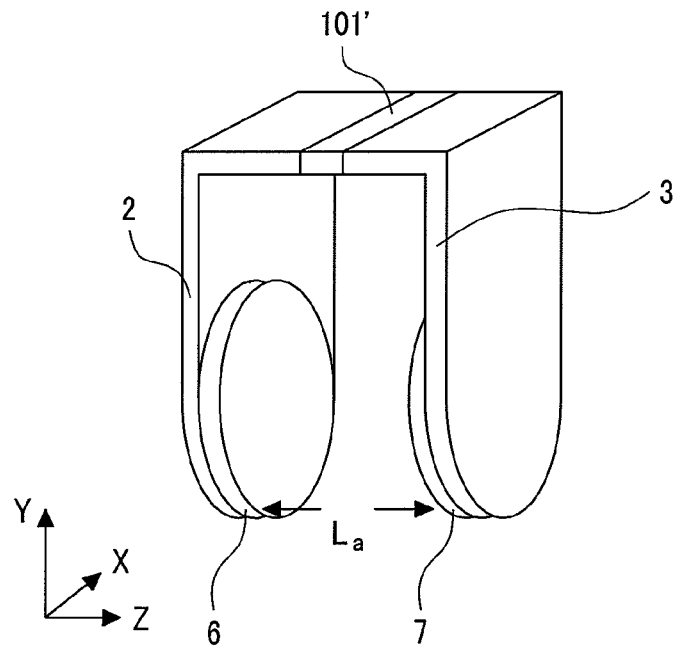
FIGS. 9A and 9B are diagrams showing still another embodiment of a magnetic system by a permanent magnet which forms a magnetic space.
Figure 9B:
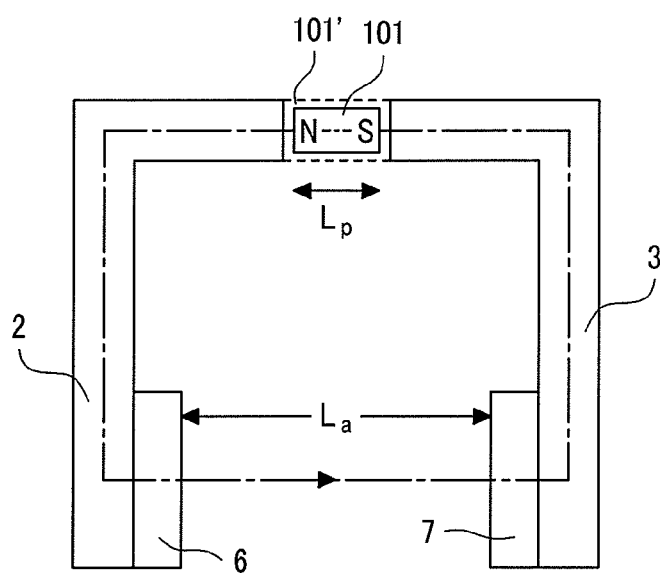
Figure 10:
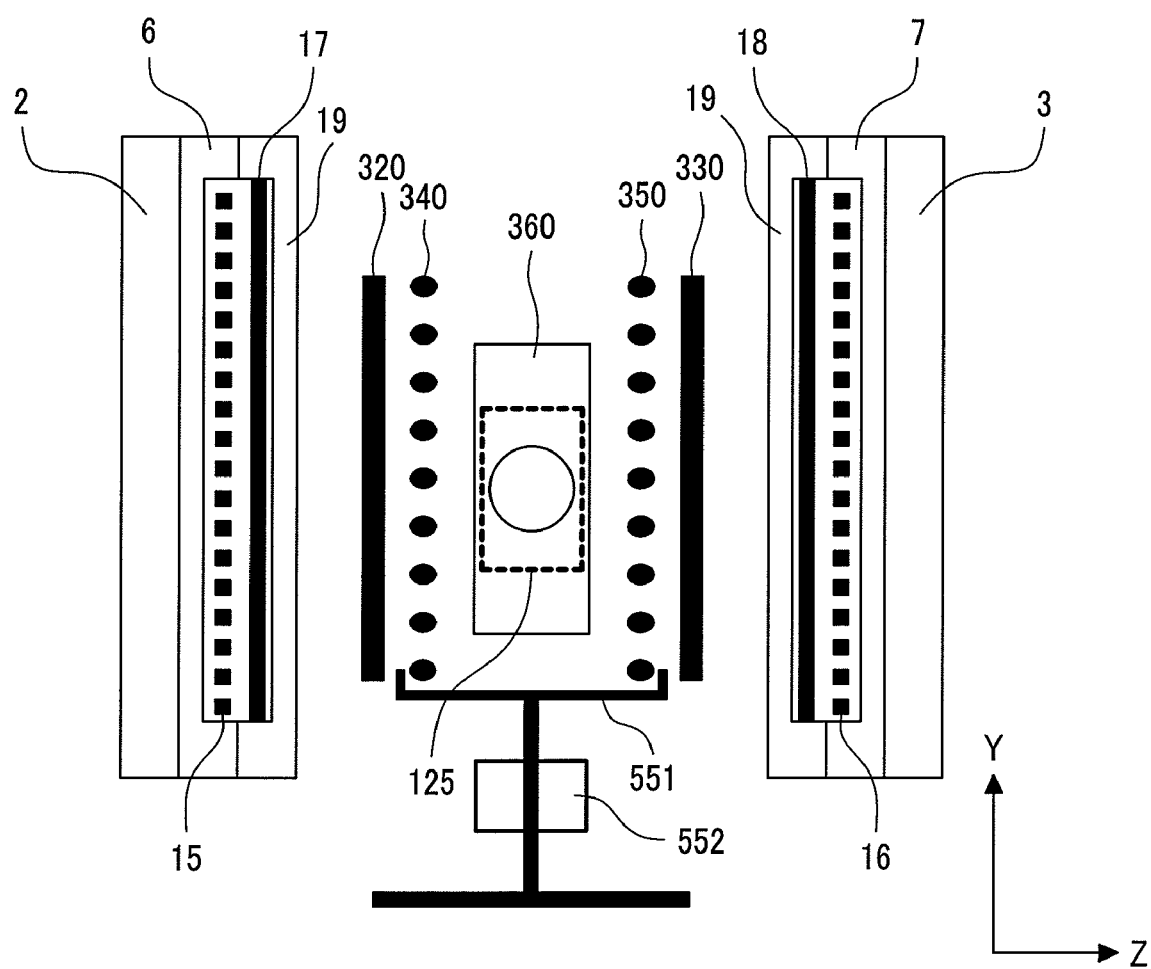
FIG. 10 is a diagram illustrating a method of moving a gradient coil system in a magnetic space.

Another embodiment having the basic concept of the present invention is shown below. A second embodiment is ESR-CT targeting a rat which is fairly larger than a mouse. For the second embodiment, technical examples regarding 400-MHz ESR-CT including a movable gradient coil system are shown in FIG. 9A, FIG. 9B, and FIG. 10. The main part of the appearance of the permanent magnet system is shown in FIG. 9A, and a magnetic circuit loop on the Y-Z plane taken along a magnetic line passing the permanent magnet system 101' is shown by a dashed line in FIG. 9B. In FIG. 9A, the magnet of the permanent magnet system is installed on the X-Z plane, and portions which support the yokes 2 and 3 from outside are omitted. FIG. 10 is a sectional view showing coil arrangements of the permanent magnet system in the magnet field, taken at the center of the permanent magnet 101 and viewed along the X axis. Like the first embodiment shown in FIG. 5, the present embodiment includes a stage 551 which mounts the gradient coil system and an apparatus 552 which moves the gradient coil system toward the X, Y, and Z directions, as shown in FIG. 10. The coil arrangements of the present embodiment differ from those of the first embodiment in that there is no yoke in the −Y direction making it possible to secure a wide space for installing the stage 551 which mounts the gradient coil system and the apparatus 552 which moves the gradient coil system toward the X, Y, and Z directions. Of course, it goes without saying that the movable gradient coil system can be arranged also with arrangements of the first embodiment.

In FIG. 10, the same components as those in FIG. 5 and FIG. 8 are assigned the same reference numerals. Although the pair of Helmholtz coils 320 and 330 and the RF probe system 360 are fixed to the pole piece cover 19 with a non-magnetic instrument, these are not shown in FIG. 10 like FIG. 8. A reference numeral 125 is a field modulation coil which is used for CW-based ESR-CT when applying field strength modulation of several kHz to 50 kHz on field strength scanning by Helmholts coils. Like the first embodiment, the present embodiment is used to improve the sensitivity of CW-based ESR by measuring a differential value of the ESR absorption curve. Since the present embodiment targets a rat which is fairly larger than a mouse, the measured space L (a region subjected to imaging, such as the rat) was set to 40 mm.

The diameter of the pole pieces 6 and 7 is 600 mm, and the distance La between the pole piece covers 19 and 20 is 300 mm. The length Ly of the yokes is set to 1500 mm; the length Lp (FIG. 9B), thickness, and height h of the permanent magnet are set to 60 mm, 25 mm, and 400 mm, respectively. A relative magnetic permeability $\mu/\mu_0$ of an iron yoke is about 1000. The thickness and the height h of the iron yokes 2 and 3 are 40 mm and 600 mm, respectively. The structure of the permanent magnet system 101' is the same as that of the permanent magnet system 1' of FIG. 7B, which performs temperature control of the permanent magnet 101.

Since a Samarium Cobalt magnet has a coersive force Hc of 1591 kA/m and a residual magnetic flux density Br of about 11,000 G, Formula (7) is applied to a case when the permanent magnet and the yokes on both sides thereof have the same height (600 mm) in a magnetic circuit. This is equivalent to a magnetic field strength of about 2780 G using the magnetic field strength $H_G$ (hereinafter simply referred to as magnetic field strength) defined from the flux density $Bp(=\mu_0 H_G)$ on the surface of the opposed pole pieces. Formula (7) does not take into consideration the junction area between the permanent magnet and the yokes and the area of the pole pieces. If this area ratio $S_M/S_a$ of about 1/18.9 is taken into consideration, $H_G$ becomes 147.5 G from Formula (2) which is close to the target value 142.8 G. Based on this coarse estimate, specific dimensions were selected through computer simulation using a magnetic circuit with the actual shape inputted. Then, shimming was performed using magnet pieces 15 and 16 to obtain the following uniform magnetic field distribution, where the measured space L (a region subjected to imaging, such as a mouse) is 40 mm. The temperature coefficient of a space having a uniform static magnetic field was −318 ppm/° C. when the room temperature was 25° C.

At the center of the static magnetic space formed between the opposed pole pieces 6 and 7, a measured space (a region subjected to imaging), i.e., a space in which a subject for ESR-CT is arranged, having a uniform magnetic field and little time variation is formed.

If the gradient field coil is made movable, it is necessary to align the center of static field strength with the origin of the gradient field strength in advance. To accomplish this object, the center of the static field known from the design of the permanent magnet is aligned with the origin of the gradient field known from the design of the gradient coil system in advance, and then ESR resonance of a material having a small absorption width of 20 mG is measured, allowing both origins to be corrected. Usually, the above-mentioned origins can be aligned with an accuracy of 1 mm or less.

The gradient coil system of FIG. 10 is fixed to the non-magnetic fixing instrument 551, and the apparatus 552 which can move the gradient coil system toward the X, Y, and Z directions through personal computer control. This apparatus 552 moves the gradient coil system toward the X, Y, and Z directions in 50-μm steps by means of a stepping motor.

The interval Lsc (magnetic space) between the opposed Helmholtz coils 320 and 330 is 170 mm, the interval $L_{GC}$ (magnetic space) between the opposed gradient field coils 340 and 350 installed in Lsc is 125 mm, and the width Lpb of the RF probe system 360 is 70 mm; the width being determined by the width of an RF shield box including transmit and receive coils and the field modulation coil 125. The inner diameter R of the receive coil of the RF probe system 360 is 48 mm. The thickness of each of the pair of gradient field coils 340 and 350 and the pair of Helmholtz coils 320 and 330 (thickness of coils when the coils are implemented in a non-magnetic substrate) is 5 mm, and the width $L_{GC}'$ of the pair of gradient field coils 340 and 350 is 135 mm. These values satisfy Formula (28). The thus-configured large distance between the pole pieces makes it possible to form the RF probe system, the gradient coil system, and the field scanning coil system between the pole pieces with lot of margins, allowing high-speed response of the gradient coil system and the field scanning coil system and accordingly high-speed imaging of a small animal, such as a rat.

In accordance with the second embodiment, the magnitude L of the sample space (magnitude of the space having a uniform magnetic field in the receive coil) is 40 mm and the distance La between the pole pieces is 300 mm, giving a ratio L/La of 0.133. Like the first embodiment, a space between the pole pieces which is 5.25 to 6.75 times larger than that with conventional technology can be realized.

The scanning field strength Hs is 3.5 G, and ΔHs represented by Formula (11) is as small as 3.7 mG, sufficiently satisfying the condition of Formula (3). The pair of Helmholtz coils 320 and 330 is separated from the end faces of the pole pieces by about 60 mm, allowing effect of eddy current to be ignored.

A circular mark on the RF probe 360 shows a space into which a rat is inserted. The diameter of this space is 44 mm. The RF probe 360 has a width of 70 mm and a space of 27.5 mm on both sides thereof toward the pair of gradient field coils 340 and 350. The XYZ stage 551 is designed so as to move over a range of 25 mm in the X, Y, and Z directions, and a range of 20.0 mm therein, a half of the magnitude L of the measured space from the center, in 50-μm steps.

An example of improved spatial resolution by movable gradient field coils will be explained below. When the gradient field strength G is 2 G/cm and the line width ΔH of a contrast agent to be applied to a mouse is 20 mG, the theoretical spatial resolution was 0.1 mm, the Q value was 80, and the magnitude of the measured space was 40 mm. Therefore, $L_0$ is 8.9 mm from Formula (21), and the number of splits n in space in the X, Y, and Z-axis directions becomes 8 from Formula (25). By moving the origin of the gradient coil system to the maximum spatial split point $8^3$ (512 spatial split points), it was possible to image the entire measured space with a spatial resolution of 0.1 mm. However, there are not so many cases when it is necessary to image the entire measured space with a magnitude of 40 mm with a spatial resolution of as high as 0.1 mm. Therefore, high-resolution images are obtained by moving the origin of the gradient coil system only to necessary spatial split points, which is referred to as zoom-in function.

400-MHz CW-based ESR-CT is well characterized by a configuration in which a magnetic space is formed by a permanent magnet. The present embodiment performs field strength scanning by use of a carrier wave amplifier which generates a secondary magnetic field strength Hs from the pair of Helmholtz coils 320 and 330 and a carrier wave generator which vibrates the frequency of the carrier wave amplifier at high speed (up to 5 kHz). 50-kHz field strength modulation is applied to the field modulation coil 125 on this field scanning. The modulation field strength can be set within a range from ±3.5 mG to ±100 mG. Assuming that the maximum value of relaxation time T1 of the radical under measurement is 10 to 20 μs, it is necessary to set a frequency which is not more than the reciprocal of the relaxation time T1 and therefore a frequency of 50 kHz was chosen. An AFC (Automatic Frequency Control) circuit which conforms a 400-MHz oscillation frequency to the resonance frequency is driven by 35 kHz. A 400-MHz RF oscillator is provided with a 35-kHz FM modulation function, and the gradient field coils 340 and 350 are controlled by a DSP (digital signal processor).

The present CW-ESR-CT is characterized in that ultra-high-speed scanning with up to 5 kHz was enabled because a magnetic field structure by a permanent magnet was used for field strength Hs scanning, allowing a mouse in a 40-mm measured space to be imaged for about 13 minutes and remarkably reducing the observation time of ESR-CT.

Like the above-mentioned second embodiment, a sample can be adjusted to a desired location by moving the gradient coil system. Therefore, a zoom-in function was realized with a spatial resolution of 1 mm or less with an ESR-CT apparatus by choosing a desired location like the object of the present invention.

Third Embodiment

Another embodiment of the zoom-in function of the present invention will be explained below as a third embodiment.

Figure 11:
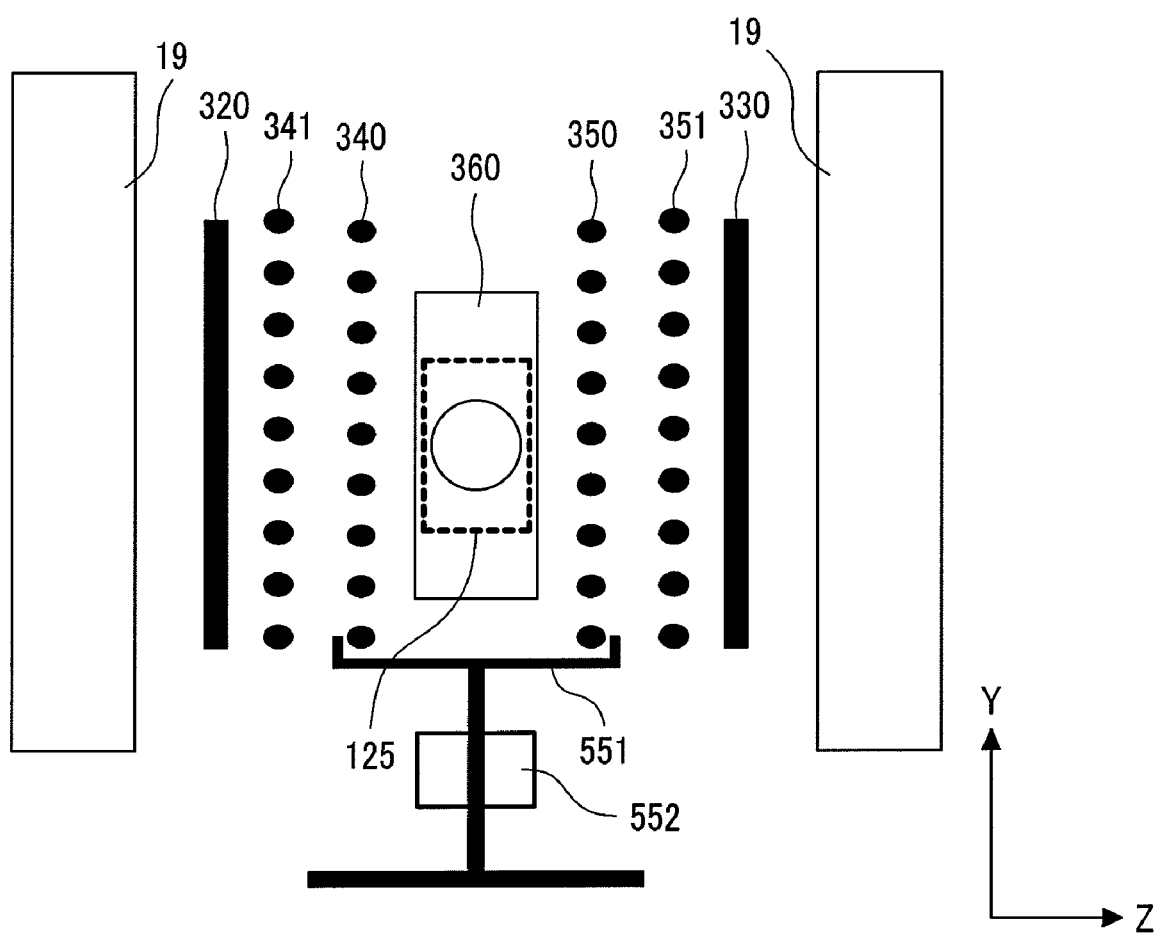
FIG. 11 is a diagram showing another embodiment of a movable gradient field system.

The third embodiment is another embodiment of the second embodiment. The third embodiment uses the same permanent magnet system as the second embodiment and differs therefrom in that the gradient coil system formed between the pole pieces include both a fixed gradient coil system and a movable gradient coil system. FIG. 11 is a sectional view showing coil arrangements corresponding to FIG. 10 of the second embodiment. The present embodiment will be explained below centering on differences from the second embodiment.

Unlike the second embodiment, the third embodiment is characterized in that it is provided with a pair of fixed gradient field coils 341 and 351 which images mainly the entire measured space and a pair of movable gradient field coils 340 and 350 which is in charge of the zoom-in function and has a small region subjected to imaging and a large gradient field strength. Like the second embodiment, the pair of movable gradient field coils 340 and 350 is connected with the fixing stage 551 and the movable system 552 thereof. In FIG. 11, the same reference numerals as those of FIG. 10 correspond to the parts having the same function. The yokes, the permanent magnet, and the pole pieces shown in FIG. 10 are omitted. Since the fixed gradient coil system images the entire measured space, it is necessary to guarantee the linearity of the gradient magnetic field to, for example, ±2% or less over the entire measured space, resulting in a relatively large-sized coil system. However, since the movable gradient coil system has a large gradient field strength and a magnitude of measurement space which is in inverse proportion to the gradient field strength, a space which guarantees the linearity of the gradient magnetic field may be small, allowing the coil system to be downsized.

The interval Lsc (magnetic space) between the opposed Helmholtz coils 320 and 330 is 190 mm, the interval $L_{GC}$ (magnetic space) between the movable gradient field coils 340 and 350 installed in Lsc is 125 mm, the interval $L_{GC2}$ (magnetic space) between the opposed fixed gradient field coils 341 and 351 is 160 mm, the thickness of each of the pairs of gradient field coils 340, 350, 341, and 351 and the pair of Helmholtz coils 320 and 330 (thickness of system when the coils are implemented in a non-magnetic substrate) is 5 mm, and the width $L_{GC}'$ of the pair of gradient field coils 340 and 350 is 135 mm. These values satisfy Formula (28). In this case, however, the interval $L_{GC2}$ between the opposed fixed gradient field coils 341 and 351 substitutes for the interval Lsc between the opposed Helmholtz coils 320 and 330 of Formula (29). In this case, the pair of Helmholtz coils 320 and 330 is apart from the end faces of the pole pieces by 50 mm or more, allowing effect of eddy current to be ignored. The diameter of the pair of Helmholtz coils 320 and 330 is 380 mm, and the diameter of the pair of fixed gradient field coils 341 and 351 is 460 mm. Although the region in which a guaranteed linearity of the movable gradient system by the pair of gradient field coils 340 and 350 is ±2% or less has been reduced to about 20 mm, the pair of fixed gradient field coils 340 and 350 can be implemented in a disc with a diameter of 200 mm, allowing compact design of the fixing stage 551 and the movable system 552 thereof.

By separating the roles of the fixed gradient coil system and the movable gradient coil system, the movable gradient coil system, the fixing stage 551, and the movable system 552 thereof can be provided as options for a case when high-resolution images are occasionally required, resulting in improved operability. Furthermore, since the movable gradient coil system can be downsized, a stronger gradient magnetic field can be provided with the same current, providing ultrahigh-resolution images.

In some cases, it is also possible to make two pairs of fixed gradient coil systems and perform different kinds of imaging in terms of the difference in the gradient magnetic field strength (difference in zooming magnification).

The above explanation has shown that diverse functions which have been impossible can be realized by securing a wide gap between the pole pieces.

In accordance with the present invention, the use of the zoom-in function has made it possible to obtain clear images also for a radical having a large absorption width ΔH with several Gauss, as mentioned in the second and third embodiments.

In accordance with the first and second embodiments, although embodiments regarding ESR-CT of 200 MHz (equivalent to a magnetic field strength of 71.4 G) and 400 MHz (equivalent to a magnetic field strength of 142.8 G) have been disclosed, ESR-CT of up to about 1200 MHz (430 G) can similarly be applied to the living body. On the other hand, the present invention is also applicable to other than the living body (target with little ESR signal attenuation by water). In this case, the present RF probe can be applied to up to about 1050 G (about 3000 MHz) by extension.

In accordance with the present invention, the following effects have also been obtained.

(1) With the use of a permanent magnet having a small temperature coefficient near the room temperature (for example, −300/° C. for Samarium Cobalt or −200-/° C. for AlNiCo magnet), it became unnecessary to strictly control the temperature of the room in which the magnet is installed by heating the permanent magnet portion, retaining the heat, and controlling the temperature of the permanent magnet at about 30° C.±0.01° C. A room temperature variation of about ±5° C. contributes so slightly to temperature variation of the yokes and the opposed pole pieces that it can be ignored. Therefore, it was possible to restrain long-term variation of the magnetic field strength to ±4 mG or less by accurately controlling the temperature of the permanent magnet.

(2) The 5-G line can be set to 50 cm or less from the magnet system resulting in a compact leak magnetic field region. Accordingly, the weight of the 70 G magnet system becomes about 400 kg or less resulting in a very compact system.

(3) As the static field strength increases from 70 G to 400 G, the ESR sensitivity improves by the square of the magnetic field strength. However, the present invention differs largely from an air-core magnet system in that magnetic field characteristics can be maintained by increasing the volume of the permanent magnet even if the static field strength is increased.

(4) Although the permanent magnet system requires a power supply for driving an auxiliary coil system, large current is not drawn allowing the system to be compact and lightweight.

What is claimed is:

1. An electron spin resonance CT apparatus comprising:
    pole pieces having a predetermined area $S_a$ which are opposed to each other through a space;
    yokes combined with the pole pieces;
    a permanent magnet inserted in series in a closed magnetic circuit formed by the pole pieces, the yokes, and the space between the pole pieces so that at least one magnetic pole plane intersects perpendicularly to the closed magnetic circuit; and
    a gradient coil system and an RF probe system for high-frequency transmission and reception which are formed between the pole pieces,
    wherein a magnetic system for the electron spin resonance CT apparatus is formed by the pole pieces, the yokes and the permanent magnet; and
    wherein the at least one magnetic pole plane of the permanent magnet has a small junction area which is ⅓ to 1/30 times as small as an area of opposed surfaces of the pole pieces.

2. The electron spin resonance CT apparatus according to claim 1, wherein
    the RF probe system for high-frequency transmission and reception is fixed to a predetermined position of the space between the pole pieces; and
    a stage for changing a relative position of the gradient coil system with respect to the RF probe system for high-frequency transmission and reception is provided.

3. The electron spin resonance CT apparatus according to claim 2, wherein
    a field scanning coil system which performs field scanning of a static magnetic field is formed between the pole pieces;
    an interval $L_{GC}$ between the opposed gradient field coils is larger than a width Lpb of the RF probe system for high-frequency transmission and reception;
    an interval $L_{SC}$ between the opposed field scanning coils is larger than the interval $L_{GC}$ between the opposed gradient field coils; and
    a distance La between the opposed pole pieces is a sum of the interval $L_{SC}$ of the opposed field scanning coils and a predetermined distance.

4. The electron spin resonance CT apparatus according to claim 2, wherein
    the interval $L_{GC}$ between the opposed gradient field coils is formed between the pole piece so that the interval $L_{GC}$ is larger than the width Lpb of the RF probe system for high-frequency transmission and reception; and
    the distance La between the pole pieces is a sum of the interval $L_{GC}$ of the opposed gradient field coils and a predetermined distance.

5. The electron spin resonance CT apparatus according to claim 3, wherein
    the interval $L_{GC}$ between the opposed gradient field coils is larger than a sum of an inner diameter R of a receive coil and the width Lpb of the RF probe system; and
    a sum of the interval $L_{SC}$ between the opposed field scanning coils and the width Lpb of the RF probe system is larger than a sum of the interval $L_{GC}$ between the opposed gradient field coils and the width $L_{GC}'$ of the pair of the gradient field coils.

6. The electron spin resonance CT apparatus according to claim 4, wherein
    the interval $L_{GC}$ between the opposed gradient field coils is larger than a sum of the inner diameter R of the receive coil and the width Lpb of the RF probe system; and
    a sum of the distance La between the pole pieces and the width Lpb of the RF probe system is larger than a sum of the interval $L_{GC}$ between the opposed gradient field coils and the width $L_{GC}'$ of the pair of gradient field coils.

7. The electron spin resonance CT apparatus according to claim 4, wherein a distance from end faces of the pole pieces to the field scanning coils is 50 mm or more.

8. The electron spin resonance CT apparatus according to claim 5, wherein a distance from end faces of the pole pieces to the field scanning coils is 50 mm or more.

9. The electron spin resonance CT apparatus according to claim 4, wherein a static magnetic field formed between the end faces of the pole pieces is 70 G to 1050 G.

10. The electron spin resonance CT apparatus according to claim 5, wherein a static magnetic field formed between the end faces of the pole pieces is 70 G to 1050 G.

11. The electron spin resonance CT apparatus according to claim 4, comprising:

control means for maintaining the permanent magnet at a temperature higher than the room temperature.

12. The electron spin resonance CT apparatus according to claim 5, comprising:

control means for maintaining the permanent magnet at a temperature higher than the room temperature.

13. The electron spin resonance CT apparatus according to claim 11, wherein an absolute value of a temperature coefficient of the permanent magnet is 400 ppm/° C. or less.

14. The electron spin resonance CT apparatus according to claim 12, wherein an absolute value of a temperature coefficient of the permanent magnet is 400 ppm/° C. or less.

15. The electron spin resonance CT apparatus according to claim 13, wherein the permanent magnet is a Samarium Cobalt magnet.

16. The electron spin resonance CT apparatus according to claim 14, wherein the permanent magnet is a Samarium Cobalt magnet.

17. The electron spin resonance CT apparatus according to claim 1, wherein the permanent magnet consists of a plurality of blocks of magnets.

* * * * *